United States Patent
Albrecht et al.

(10) Patent No.: US 9,174,991 B2
(45) Date of Patent: Nov. 3, 2015

(54) CRYSTALLINE FORM OF PEMETREXED DISODIUM

(75) Inventors: Uwe Jens Albrecht, Basel (CH); Hannes Helmboldt, Chemnitz (DE); Vsevolod Valerievich Nikolaev, Zürch (CH)

(73) Assignees: Azad Pharmaceutical Ingredients AG, Schaffhausen (CH); University of Zurich, Zurich (CH)

(*) Notice: Subject to any disclaimer, the term of this patent is extended or adjusted under 35 U.S.C. 154(b) by 484 days.

(21) Appl. No.: 13/511,723

(22) PCT Filed: Nov. 24, 2010

(86) PCT No.: PCT/EP2010/068132
§ 371 (c)(1),
(2), (4) Date: Sep. 7, 2012

(87) PCT Pub. No.: WO2011/064256
PCT Pub. Date: Jun. 3, 2011

(65) Prior Publication Data
US 2012/0329819 A1    Dec. 27, 2012

Related U.S. Application Data

(60) Provisional application No. 61/264,018, filed on Nov. 24, 2009.

(51) Int. Cl.
C07D 487/04    (2006.01)
A61K 31/519    (2006.01)
A61P 35/00    (2006.01)

(52) U.S. Cl.
CPC ............................ *C07D 487/04* (2013.01)

(58) Field of Classification Search
CPC .......................... C07D 487/04; A61K 31/519
USPC ........................................ 544/280; 514/265.1
See application file for complete search history.

(56) References Cited

FOREIGN PATENT DOCUMENTS

| WO | 01/14379 A2 | 3/2001 |
|---|---|---|
| WO | 01/62760 A2 | 8/2001 |
| WO | 2008/124485 A2 | 10/2008 |

OTHER PUBLICATIONS

Bhattacharya et al. (Brittain, ed. Polymorphism in Pharmaceutical Solids, 2009, p. 334.*
Barnett et al., "A practical synthesis of multitargeted antifolate LY231514", Organic Process Research and Development, vol. 3, No. 3, Jan. 1, 1999, pp. 184-188.
Li et al., "Pemetrexed pharmacokinetics and phamacodynamics in a phase I/II study of doublet chemotherapy with vinorelbine: implications for further optimisation of pemetrexed schedules", British Journal of Cancer (2007) 97, 1071-1076.

* cited by examiner

*Primary Examiner* — Susanna Moore
(74) *Attorney, Agent, or Firm* — Rothwell, Figg, Ernst & Manbeck, P.C.

(57) ABSTRACT

The present invention relates to a new polymorphic or crystalline form of Pemetrexed Disodium, processes for its preparation and its use, in particular for the preparation of medicaments.

33 Claims, 30 Drawing Sheets

PXRD-profile of Pemetrexed Disodium Form IV

Figure 1B

Figure 1A:
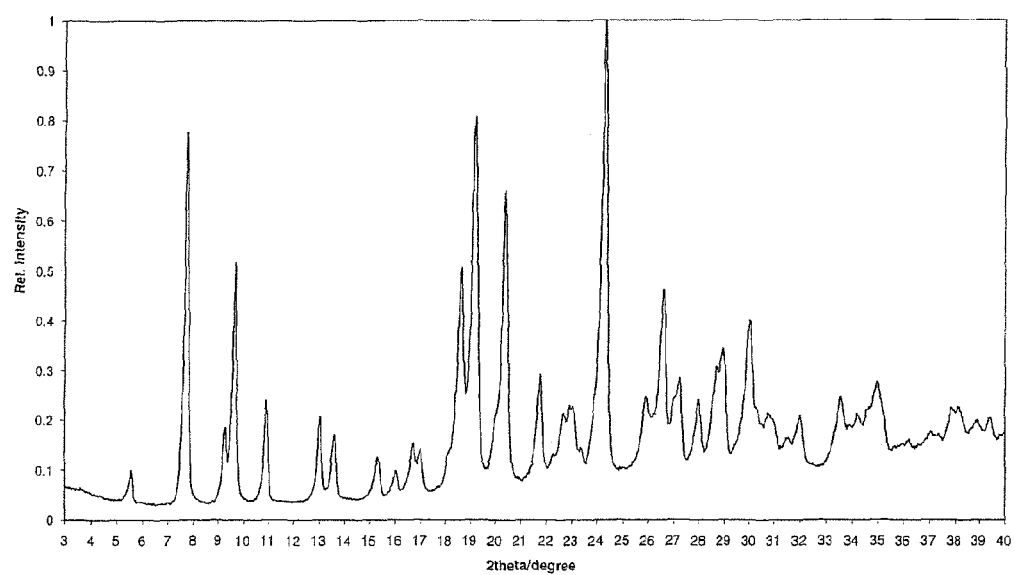

| Pos. [°2Th.] | d-spacing [Å] | Intensity [cts] | Rel. Int. [%] |
|---|---|---|---|
| 5.53 | 15.98 | 3624 | 9.8 |
| 7.72 | 11.44 | 28567 | 77.6 |
| 9.23 | 9.57 | 6810 | 18.5 |
| 9.65 | 9.16 | 18929 | 51.4 |
| 10.91 | 8.10 | 8798 | 23.9 |
| 13.04 | 6.79 | 7552 | 20.5 |
| 13.59 | 6.51 | 6313 | 17.2 |
| 15.32 | 5.78 | 4590 | 12.5 |
| 16.03 | 5.52 | 3578 | 9.7 |
| 16.72 | 5.30 | 5650 | 15.4 |
| 16.99 | 5.21 | 5170 | 14.0 |
| 18.12 | 4.89 | 4978 | 13.5 |
| 18.61 | 4.77 | 18613 | 50.6 |
| 19.18 | 4.62 | 29691 | 80.7 |
| 19.98 | 4.44 | 7835 | 21.3 |
| 20.39 | 4.35 | 24226 | 65.8 |
| 21.75 | 4.08 | 10720 | 29.1 |
| 22.27 | 3.99 | 4873 | 13.2 |
| 22.67 | 3.92 | 7865 | 21.4 |
| 23.04 | 3.86 | 8371 | 22.7 |
| 24.29 | 3.66 | 36806 | 100.0 |
| 25.93 | 3.43 | 9072 | 24.6 |
| 26.58 | 3.35 | 16973 | 46.1 |
| 27.01 | 3.30 | 9088 | 24.7 |
| 27.20 | 3.28 | 10435 | 28.4 |
| 27.98 | 3.19 | 8831 | 24.0 |
| 28.68 | 3.11 | 11287 | 30.7 |
| 28.93 | 3.08 | 12624 | 34.3 |
| 30.01 | 2.98 | 14727 | 40.0 |
| 30.78 | 2.90 | 7896 | 21.5 |
| 31.52 | 2.84 | 6030 | 16.4 |
| 31.98 | 2.80 | 7687 | 20.9 |
| 33.57 | 2.67 | 9036 | 24.6 |
| 34.21 | 2.62 | 7789 | 21.2 |
| 34.63 | 2.59 | 8303 | 22.6 |
| 34.96 | 2.56 | 10142 | 27.6 |
| 36.21 | 2.48 | 5900 | 16.0 |
| 37.07 | 2.42 | 6494 | 17.6 |
| 37.88 | 2.37 | 8250 | 22.4 |
| 38.18 | 2.36 | 8328 | 22.6 |
| 38.90 | 2.31 | 7358 | 20.0 |
| 39.41 | 2.28 | 7488 | 20.3 |

PXRD data of Pemetrexed Disodium Form IV

Figure 2B

| No. | Position [cm-1] | Intensity [%T] | No. | Position [cm-1] | Intensity [%T] |
|---|---|---|---|---|---|
| 1 | 3469.31 | 84.84 | 29 | 1287.25 | 50.21 |
| 2 | 3420.14 | 90.43 | 30 | 1248.68 | 71.12 |
| 3 | 3406.64 | 94.12 | 31 | 1227.47 | 64.38 |
| 4 | 3388.32 | 88.03 | 32 | 1212.04 | 70.46 |
| 5 | 3306.36 | 76.47 | 33 | 1181.19 | 76.38 |
| 6 | 3206.08 | 79.94 | 34 | 1160.94 | 79.20 |
| 7 | 3098.08 | 87.24 | 35 | 1149.37 | 77.67 |
| 8 | 2925.48 | 83.10 | 36 | 1139.72 | 79.91 |
| 9 | 2901.38 | 83.58 | 37 | 1105.01 | 78.28 |
| 10 | 2866.67 | 83.64 | 38 | 1092.48 | 76.98 |
| 11 | 2751.92 | 83.93 | 39 | 1080.91 | 75.03 |
| 12 | 2364.30 | 94.82 | 40 | 1040.41 | 80.52 |
| 13 | 2354.66 | 94.39 | 41 | 1018.23 | 77.27 |
| 14 | 2322.84 | 94.66 | 42 | 999.91 | 83.82 |
| 15 | 2291.98 | 95.15 | 43 | 949.77 | 87.91 |
| 16 | 2164.70 | 96.35 | 44 | 902.52 | 69.91 |
| 17 | 1984.39 | 96.86 | 45 | 876.49 | 72.95 |
| 18 | 1691.27 | 54.63 | 46 | 859.13 | 64.76 |
| 19 | 1640.16 | 41.55 | 47 | 845.63 | 68.85 |
| 20 | 1610.27 | 45.62 | 48 | 819.60 | 65.02 |
| 21 | 1575.56 | 21.49 | 49 | 778.14 | 56.72 |
| 22 | 1530.24 | 44.44 | 50 | 760.78 | 62.56 |
| 23 | 1519.63 | 42.48 | 51 | 740.53 | 60.06 |
| 24 | 1489.74 | 44.48 | 52 | 715.46 | 75.00 |
| 25 | 1454.06 | 48.27 | 53 | 705.82 | 64.34 |
| 26 | 1408.75 | 38.54 | 54 | 689.43 | 68.00 |
| 27 | 1393.32 | 41.42 | 55 | 675.93 | 47.03 |
| 28 | 1348.00 | 63.24 | | | |

FT-IR data of Pemetrexed Disodium Form IV

Figure 4

| d value (Å) of Disodium MTA Hydrate Form I (patent data) | calculated 2theta values | I/Io (patent data) |
|---|---|---|
| 18.66 | 4.73 | 100 |
| 11.38 | 7.76 | 18 |
| 9.33 | 9.47 | 69 |
| 8.71 | 10.15 | 11 |
| 8.44 | 10.47 | 24 |
| 6.22 | 14.23 | 28 |
| 5.92 | 14.95 | 17 |
| 5.69 | 15.56 | 55 |
| 5.59 | 15.84 | 10 |
| 5.14 | 17.24 | 11 |
| 4.92 | 18.01 | 49 |
| 4.75 | 18.67 | 24 |
| 4.66 | 19.03 | 22 |
| 4.59 | 19.32 | 16 |
| 4.26 | 20.83 | 12 |
| 3.87 | 22.96 | 52 |
| 3.8 | 23.39 | 12 |
| 3.72 | 23.90 | 38 |
| 3.43 | 25.96 | 19 |
| 3.29 | 27.08 | 25 |
| 3.13 | 28.49 | 10 |
| 3.11 | 28.68 | 16 |
| 3.08 | 28.97 | 18 |
| 2.95 | 30.27 | 11 |

PXRD peak listing of Disodium MTA Hydrate Fo
application no. 0114379) (note: 2theta values have been calculated from d-spacing values based on Cu wave length λ = 1.54056 Å)

Figure 5

| d value (Å) of Pemetrexed Disodium 7 hydrate (patent data) | calculated 2theta values | I/Io (patent data) |
|---|---|---|
| 21.6 | 4.09 | 34 |
| 11.71 | 7.54 | 15 |
| 7.78 | 11.36 | 100 |
| 7.22 | 12.25 | 15 |
| 6.29 | 14.07 | 31 |
| 5.86 | 15.11 | 21 |
| 5.6 | 15.81 | 44 |
| 5.42 | 16.34 | 34 |
| 5.26 | 16.84 | 37 |
| 5.1 | 17.37 | 43 |
| 4.79 | 18.51 | 10 |
| 4.66 | 19.03 | 84 |
| 3.91 | 22.72 | 44 |
| 3.87 | 22.96 | 14 |
| 3.83 | 23.20 | 10 |
| 3.72 | 23.90 | 69 |
| 3.62 | 24.57 | 31 |
| 3.41 | 26.11 | 24 |
| 3.24 | 27.51 | 14 |
| 3.22 | 27.68 | 36 |
| 3.12 | 28.59 | 38 |
| 3.09 | 28.87 | 47 |
| 2.97 | 30.06 | 26 |
| 2.97 | 30.06 | 21 |
| 2.91 | 30.70 | 19 |
| 2.91 | 30.70 | 16 |
| 2.69 | 33.28 | 11 |
| 2.67 | 33.54 | 11 |

PXRD peak listing of Pemetrexed Disodium 7 Hydrate described in WO patent no. 01/62760 (note: 2theta values have been calculated from d-spacing values based on Cu wave length $\lambda = 1.54056$ Å)

Figure 6

| d value (Å) of Pemetrexed Disodium 3 hydrate (patent data) | calculated 2theta values | I/Io (patent data) |
|---|---|---|
| 33 | 2.68 | 11 |
| 19.18 | 4.60 | 21 |
| 11.57 | 7.63 | 22 |
| 9.51 | 9.29 | 39 |
| 8.62 | 10.25 | 24 |
| 7.87 | 11.23 | 11 |
| 6.3 | 14.05 | 25 |
| 5.99 | 14.78 | 26 |
| 5.74 | 15.42 | 60 |
| 5.15 | 17.20 | 28 |
| 4.96 | 17.87 | 62 |
| 4.82 | 18.39 | 47 |
| 4.65 | 19.07 | 38 |
| 4.28 | 20.74 | 18 |
| 3.9 | 22.78 | 100 |
| 3.74 | 23.77 | 80 |
| 3.45 | 25.80 | 39 |
| 3.31 | 26.91 | 29 |
| 3.24 | 27.51 | 18 |
| 3.14 | 28.40 | 33 |
| 3.11 | 28.68 | 49 |
| 2.97 | 30.06 | 23 |
| 2.58 | 34.74 | 11 |
| 2.6 | 34.47 | 16 |
| 2.29 | 39.31 | 17 |

PXRD peak listing of Pemetrexed Disodium Hydrate described in CN patent no. 1778802 (note: 2theta values have been calculated from d-spacing values based on Cu wave length $\lambda = 1.54056$ Å)

Figure 7

| d value (Å) of Pemetrexed Disodium Form III (patent data) | 2theta values (patent data) | I/Io (patent data) |
| --- | --- | --- |
| 21.9 | 4 | 25.9 |
| 19.8 | 4.4 | 18.5 |
| 11.2 | 7.8 | 4.3 |
| 9.4 | 9.3 | 6.6 |
| 6.9 | 12.6 | 3.2 |
| 5.1 | 17.2 | 21.7 |
| 4.9 | 18 | 100 |
| 4.5 | 19.4 | 21 |
| 4.3 | 20.3 | 33.5 |
| 4.2 | 21 | 66.1 |
| 3.6 | 24.2 | 2.3 |
| 3.4 | 25.9 | 17.2 |
| 3.2 | 27.5 | 14.2 |
| 3 | 29 | 16 |
| 2.4 | 36.2 | 4.7 |
| 2 | 43.2 | 41.4 |

PXRD peak listing of Pemetrexed Disodium Form III described in WO patent no. 2008124485

PXRD-profile of Pemetrexed Disodium Heptahydrate

Figure 8B

| Pos. [°2Th.] | d-spacing [Å] | Intensity [cts] | Rel. Int. [%] |
|---|---|---|---|
| 4.15 | 21.27 | 33156 | 57.4 |
| 7.58 | 11.66 | 4274 | 7.4 |
| 8.78 | 10.06 | 2510 | 4.3 |
| 11.41 | 7.75 | 57769 | 100.0 |
| 12.31 | 7.19 | 15235 | 26.4 |
| 14.12 | 6.27 | 17467 | 30.2 |
| 15.14 | 5.85 | 10446 | 18.1 |
| 15.86 | 5.58 | 21778 | 37.7 |
| 16.41 | 5.40 | 39640 | 68.6 |
| 16.88 | 5.25 | 16047 | 27.8 |
| 17.38 | 5.10 | 7871 | 13.6 |
| 18.50 | 4.79 | 5058 | 8.8 |
| 19.05 | 4.65 | 28616 | 49.5 |
| 19.99 | 4.44 | 6426 | 11.1 |
| 20.53 | 4.32 | 6210 | 10.7 |
| 21.54 | 4.12 | 8893 | 15.4 |
| 22.25 | 3.99 | 13384 | 23.2 |
| 22.75 | 3.91 | 16496 | 28.6 |
| 23.88 | 3.72 | 29575 | 51.2 |
| 24.65 | 3.61 | 25117 | 43.5 |
| 25.48 | 3.49 | 7909 | 13.7 |
| 26.19 | 3.40 | 50056 | 86.6 |
| 26.66 | 3.34 | 8398 | 14.5 |
| 27.68 | 3.22 | 19227 | 33.3 |
| 28.58 | 3.12 | 24260 | 42.0 |
| 28.89 | 3.09 | 24232 | 41.9 |
| 29.74 | 3.00 | 17019 | 29.5 |
| 30.03 | 2.97 | 27533 | 47.7 |
| 30.67 | 2.91 | 17278 | 29.9 |
| 31.26 | 2.86 | 8745 | 15.1 |
| 32.00 | 2.80 | 9113 | 15.8 |
| 33.02 | 2.71 | 15251 | 26.4 |
| 33.38 | 2.68 | 22091 | 38.2 |
| 33.54 | 2.67 | 18789 | 32.5 |
| 34.34 | 2.61 | 29282 | 50.7 |
| 34.79 | 2.58 | 31853 | 55.1 |
| 35.45 | 2.53 | 18485 | 32.0 |
| 36.36 | 2.47 | 9990 | 17.3 |
| 37.33 | 2.41 | 14907 | 25.8 |
| 37.67 | 2.39 | 17351 | 30.0 |
| 38.51 | 2.34 | 14481 | 25.1 |
| 39.59 | 2.27 | 11126 | 19.3 |
| 39.81 | 2.26 | 11106 | 19.2 |

PXRD data of Pemetrexed Disodium Heptahydrate

FT-IR profile of Pemetrexed Disodium Heptahydrate

Figure 9B

| No. | Position [cm⁻¹] | Intensity [%T] | No. | Position [cm⁻¹] | Intensity [%T] |
|---|---|---|---|---|---|
| 1 | 3577.31 | 93.60 | 25 | 1375.00 | 75.41 |
| 2 | 3491.49 | 87.17 | 26 | 1350.89 | 73.69 |
| 3 | 3423.99 | 83.46 | 27 | 1319.07 | 74.39 |
| 4 | 3390.24 | 81.88 | 28 | 1284.36 | 77.61 |
| 5 | 3366.14 | 81.50 | 29 | 1269.90 | 77.00 |
| 6 | 3221.50 | 84.90 | 30 | 1239.04 | 80.20 |
| 7 | 3064.33 | 86.34 | 31 | 1186.01 | 84.63 |
| 8 | 3005.52 | 86.96 | 32 | 1155.15 | 85.11 |
| 9 | 2965.98 | 87.37 | 33 | 1125.26 | 89.19 |
| 10 | 2857.99 | 84.49 | 34 | 1095.37 | 84.06 |
| 11 | 2792.42 | 86.27 | 35 | 1083.80 | 86.73 |
| 12 | 2725.89 | 88.71 | 36 | 1021.12 | 90.40 |
| 13 | 2356.59 | 94.86 | 37 | 1008.59 | 91.04 |
| 14 | 2326.70 | 94.48 | 38 | 953.63 | 90.85 |
| 15 | 2162.78 | 94.91 | 39 | 905.42 | 87.26 |
| 16 | 2115.53 | 96.21 | 40 | 853.35 | 78.26 |
| 17 | 1980.54 | 96.63 | 41 | 830.21 | 74.62 |
| 18 | 1666.20 | 82.24 | 42 | 809.96 | 77.82 |
| 19 | 1620.88 | 62.73 | 43 | 782.96 | 76.00 |
| 20 | 1561.09 | 63.18 | 44 | 763.67 | 76.40 |
| 21 | 1526.38 | 61.75 | 45 | 741.50 | 78.12 |
| 22 | 1506.13 | 67.63 | 46 | 728.00 | 76.90 |
| 23 | 1448.28 | 76.37 | 47 | 695.21 | 75.01 |
| 24 | 1402.00 | 70.22 | 48 | 674.00 | 68.26 |

FT-IR data of Pemetrexed Disodium Heptahydrate

DSC-profile of Pemetrexed Disodium Heptahydrate

PXRD-profile of Pemetrexed Disodium 2.5 hydrate

Figure 11B

| Pos. [°2Th.] | d-spacing [Å] | Intensity [cts] | Rel. Int. [%] |
|---|---|---|---|
| 4.77 | 18.50 | 29270 | 54.0 |
| 7.82 | 11.30 | 7530 | 13.9 |
| 9.50 | 9.30 | 20766 | 38.3 |
| 10.19 | 8.67 | 6361 | 11.7 |
| 10.52 | 8.41 | 11838 | 21.8 |
| 14.26 | 6.20 | 14633 | 27.0 |
| 15.00 | 5.90 | 12585 | 23.2 |
| 15.57 | 5.69 | 30401 | 56.1 |
| 15.90 | 5.57 | 10163 | 18.7 |
| 17.27 | 5.13 | 11353 | 20.9 |
| 18.03 | 4.91 | 34808 | 64.2 |
| 18.66 | 4.75 | 22618 | 41.7 |
| 19.06 | 4.65 | 19197 | 35.4 |
| 19.30 | 4.59 | 16094 | 29.7 |
| 20.86 | 4.25 | 13607 | 25.1 |
| 22.95 | 3.87 | 54209 | 100.0 |
| 23.44 | 3.79 | 20714 | 38.2 |
| 23.89 | 3.72 | 43875 | 80.9 |
| 25.54 | 3.49 | 15730 | 29.0 |
| 25.97 | 3.43 | 26854 | 49.5 |
| 26.65 | 3.34 | 17929 | 33.1 |
| 27.05 | 3.29 | 25462 | 47.0 |
| 27.52 | 3.24 | 14662 | 27.0 |
| 28.74 | 3.10 | 31075 | 57.3 |
| 30.25 | 2.95 | 20775 | 38.3 |
| 30.63 | 2.92 | 14365 | 26.5 |
| 31.51 | 2.84 | 12320 | 22.7 |
| 31.87 | 2.81 | 13750 | 25.4 |
| 32.21 | 2.78 | 13029 | 24.0 |
| 33.02 | 2.71 | 9471 | 17.5 |
| 33.98 | 2.64 | 14456 | 26.7 |
| 34.30 | 2.61 | 16659 | 30.7 |
| 34.67 | 2.58 | 19521 | 36.0 |
| 35.52 | 2.53 | 14773 | 27.3 |
| 35.71 | 2.51 | 14563 | 26.9 |
| 36.65 | 2.45 | 15221 | 28.1 |
| 37.40 | 2.40 | 13427 | 24.8 |
| 38.06 | 2.36 | 13144 | 24.2 |
| 39.35 | 2.29 | 24906 | 45.9 |

PXRD data of Pemetrexed Disodium 2.5 hydrate

FT-IR profile of Pemetrexed Disodium 2.5 hydrate

Figure 12B

| No. | Position [cm$^{-1}$] | Intensity [%T] | No. | Position [cm$^{-1}$] | Intensity [%T] |
|---|---|---|---|---|---|
| 1 | 3454.85 | 86.95 | 25 | 1318.11 | 68.34 |
| 2 | 3412.42 | 86.72 | 26 | 1291.11 | 65.23 |
| 3 | 3399.89 | 86.67 | 27 | 1239.04 | 77.10 |
| 4 | 3339.14 | 77.61 | 28 | 1217.83 | 81.61 |
| 5 | 2900.41 | 82.35 | 29 | 1200.47 | 79.16 |
| 6 | 2785.67 | 86.79 | 30 | 1190.83 | 79.41 |
| 7 | 2348.87 | 94.60 | 31 | 1173.47 | 82.53 |
| 8 | 2323.80 | 92.94 | 32 | 1152.26 | 81.38 |
| 9 | 2162.78 | 94.01 | 33 | 1097.30 | 80.93 |
| 10 | 2145.42 | 96.75 | 34 | 1079.94 | 74.14 |
| 11 | 2111.67 | 95.78 | 35 | 1054.87 | 83.24 |
| 12 | 2050.92 | 94.92 | 36 | 1039.44 | 85.04 |
| 13 | 1980.54 | 95.90 | 37 | 1023.05 | 84.60 |
| 14 | 1917.86 | 97.35 | 38 | 1010.52 | 85.16 |
| 15 | 1671.02 | 77.10 | 39 | 961.34 | 86.17 |
| 16 | 1599.66 | 46.23 | 40 | 949.77 | 85.39 |
| 17 | 1566.88 | 49.11 | 41 | 900.59 | 87.58 |
| 18 | 1529.27 | 47.45 | 42 | 876.49 | 85.61 |
| 19 | 1505.17 | 55.31 | 43 | 838.88 | 63.37 |
| 20 | 1442.49 | 73.51 | 44 | 781.99 | 70.25 |
| 21 | 1416.46 | 62.70 | 45 | 747.28 | 66.57 |
| 22 | 1399.10 | 55.46 | 46 | 712.57 | 69.25 |
| 23 | 1370.18 | 67.46 | 47 | 675.93 | 64.01 |
| 24 | 1353.78 | 65.66 | 48 | 659.54 | 66.05 |

DSC-profile of Pemetrexed Disodium Form 2.5 hydrate

PXRD-profile of Pemetrexed Disodium Form A

FT-IR-profile of Pemetrexed Disodium Form A

Figure 15B

| No. | Position [cm⁻¹] | Intensity [%T] | No. | Position [cm⁻¹] | Intensity [%T] |
|---|---|---|---|---|---|
| 1 | 3420.14 | 76.48 | 19 | 1343.18 | 44.70 |
| 2 | 3403.74 | 73.93 | 20 | 1296.89 | 47.55 |
| 3 | 3212.83 | 64.26 | 21 | 1226.50 | 59.78 |
| 4 | 2931.27 | 72.77 | 22 | 1188.90 | 67.54 |
| 5 | 2347.91 | 94.09 | 23 | 1154.19 | 69.50 |
| 6 | 2325.73 | 92.70 | 24 | 1078.01 | 62.44 |
| 7 | 2197.49 | 94.29 | 25 | 1052.94 | 73.52 |
| 8 | 2162.78 | 93.45 | 26 | 1044.26 | 74.53 |
| 9 | 2146.38 | 97.29 | 27 | 1035.59 | 76.78 |
| 10 | 2111.67 | 96.05 | 28 | 1019.19 | 73.79 |
| 11 | 2050.92 | 95.77 | 29 | 904.45 | 78.25 |
| 12 | 1980.54 | 95.96 | 30 | 832.13 | 54.59 |
| 13 | 1627.63 | 33.42 | 31 | 782.96 | 47.30 |
| 14 | 1564.95 | 19.32 | 32 | 707.75 | 49.11 |
| 15 | 1526.38 | 26.02 | 33 | 699.07 | 46.86 |
| 16 | 1498.42 | 35.97 | 34 | 690.39 | 50.58 |
| 17 | 1452.14 | 39.61 | 35 | 670.14 | 44.80 |
| 18 | 1403.92 | 27.95 | 36 | 660.50 | 42.36 |

FT-IR data of Pemetrexed Disodium Form A

DSC-profile of Pemetrexed Disodium Form A

PXRD-profile of Pemetrexed Disodium Form III

Figure 17B

| Pos. [°2Th.] | d-spacing [A] | Intensity [cts] | Rel. Int. [%] |
| --- | --- | --- | --- |
| 3.91 | 22.61 | 13385 | 46.3 |
| 5.87 | 15.05 | 2066 | 7.1 |
| 7.53 | 11.73 | 1150 | 4.0 |
| 9.25 | 9.55 | 5659 | 19.6 |
| 9.82 | 9.00 | 2203 | 7.6 |
| 10.36 | 8.54 | 1636 | 5.7 |
| 10.89 | 8.12 | 1978 | 6.8 |
| 11.38 | 7.77 | 2372 | 8.2 |
| 11.61 | 7.62 | 2499 | 8.6 |
| 11.90 | 7.43 | 2185 | 7.6 |
| 12.50 | 7.08 | 3463 | 12.0 |
| 13.06 | 6.78 | 2089 | 7.2 |
| 13.43 | 6.59 | 2831 | 9.8 |
| 13.77 | 6.43 | 2803 | 9.7 |
| 14.68 | 6.03 | 5062 | 17.5 |
| 15.02 | 5.89 | 3318 | 11.5 |
| 15.70 | 5.64 | 15940 | 55.1 |
| 16.01 | 5.53 | 5476 | 18.9 |
| 16.23 | 5.46 | 4402 | 15.2 |
| 16.61 | 5.33 | 3554 | 12.3 |
| 17.27 | 5.13 | 7559 | 26.1 |
| 17.94 | 4.94 | 9451 | 32.7 |
| 18.33 | 4.84 | 6495 | 22.5 |
| 19.10 | 4.64 | 6971 | 24.1 |
| 19.85 | 4.47 | 10781 | 37.3 |
| 20.31 | 4.37 | 17136 | 59.3 |
| 20.60 | 4.31 | 10688 | 37.0 |
| 21.11 | 4.20 | 28921 | 100.0 |
| 21.55 | 4.12 | 6543 | 22.6 |
| 21.78 | 4.08 | 10260 | 35.5 |
| 22.39 | 3.97 | 3979 | 13.8 |
| 22.68 | 3.92 | 4335 | 15.0 |
| 23.34 | 3.81 | 5399 | 18.7 |
| 23.59 | 3.77 | 5822 | 20.1 |
| 23.88 | 3.72 | 6177 | 21.4 |
| 24.39 | 3.65 | 4366 | 15.1 |
| 24.78 | 3.59 | 4797 | 16.6 |
| 25.23 | 3.53 | 9136 | 31.6 |
| 25.52 | 3.49 | 7591 | 26.2 |
| 25.83 | 3.45 | 8155 | 28.2 |
| 26.28 | 3.39 | 7658 | 26.5 |
| 26.79 | 3.32 | 10255 | 35.5 |
| 26.98 | 3.30 | 12358 | 42.7 |
| 27.19 | 3.28 | 8609 | 29.8 |
| 27.79 | 3.21 | 11005 | 38.1 |
| 28.90 | 3.09 | 16088 | 55.6 |
| 29.39 | 3.04 | 13511 | 46.7 |

RECTIFIED SHEET (RULE 91) ISA/EP

Figure 17A:
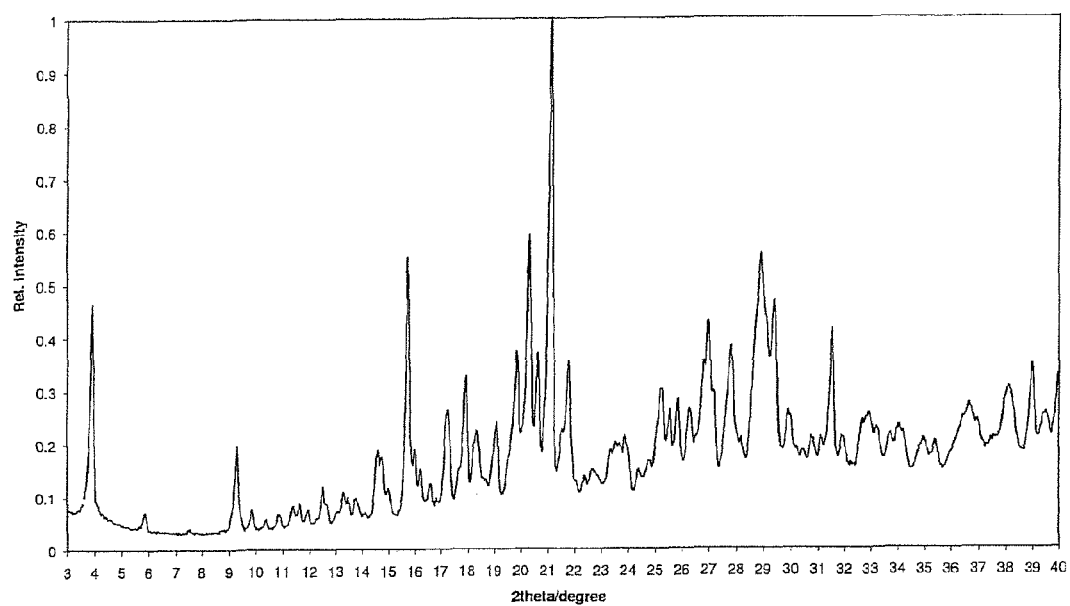

Figure 17B (continued)

| Pos. [°2Th.] | d-spacing [Å] | Intensity [cts] | Rel. Int. [%] |
|---|---|---|---|
| 29.93 | 2.98 | 7538 | 26.1 |
| 30.43 | 2.94 | 5363 | 18.5 |
| 30.78 | 2.90 | 6087 | 21.0 |
| 31.09 | 2.87 | 6068 | 21.0 |
| 31.50 | 2.84 | 11937 | 41.3 |
| 31.93 | 2.80 | 6112 | 21.1 |
| 32.81 | 2.73 | 7192 | 24.9 |
| 32.93 | 2.72 | 7396 | 25.6 |
| 33.20 | 2.70 | 6590 | 22.8 |
| 33.72 | 2.66 | 6255 | 21.6 |
| 34.03 | 2.63 | 6709 | 23.2 |
| 34.97 | 2.56 | 5983 | 20.7 |
| 35.41 | 2.53 | 5874 | 20.3 |
| 36.64 | 2.45 | 7859 | 27.2 |
| 36.96 | 2.43 | 7010 | 24.2 |
| 38.09 | 2.36 | 8801 | 30.4 |
| 38.96 | 2.31 | 10041 | 34.7 |
| 39.48 | 2.28 | 7438 | 25.7 |

PXRD data of Pemetrexed Disodium Form III

FT-IR-profile of Pemetrexed Disodium Form III

Figure 18B

| No. | Position [cm⁻¹] | Intensity [%T] | No. | Position [cm⁻¹] | Intensity [%T] |
|---|---|---|---|---|---|
| 1 | 3641.91 | 90.41 | 19 | 1268.93 | 67.64 |
| 2 | 3205.11 | 74.16 | 20 | 1229.40 | 70.97 |
| 3 | 2921.63 | 79.21 | 21 | 1188.90 | 75.36 |
| 4 | 2800.13 | 82.86 | 22 | 1154.19 | 79.88 |
| 5 | 2359.48 | 90.93 | 23 | 1110.80 | 78.89 |
| 6 | 2348.87 | 91.81 | 24 | 1075.12 | 73.35 |
| 7 | 2323.80 | 91.22 | 25 | 1018.23 | 80.46 |
| 8 | 2163.74 | 92.49 | 26 | 953.63 | 84.32 |
| 9 | 2050.92 | 93.72 | 27 | 901.56 | 80.03 |
| 10 | 1986.32 | 94.60 | 28 | 861.06 | 72.08 |
| 11 | 1637.27 | 48.55 | 29 | 823.46 | 64.17 |
| 12 | 1593.88 | 38.36 | 30 | 785.85 | 66.10 |
| 13 | 1523.49 | 41.93 | 31 | 765.60 | 63.53 |
| 14 | 1496.49 | 49.34 | 32 | 742.46 | 68.15 |
| 15 | 1407.78 | 43.77 | 33 | 713.53 | 60.76 |
| 16 | 1347.03 | 58.78 | 34 | 692.32 | 60.40 |
| 17 | 1313.29 | 60.96 | 35 | 669.18 | 60.17 |
| 18 | 1296.89 | 58.02 | | | |

FT-IR data of Pemetrexed Disodium Form III

CRYSTALLINE FORM OF PEMETREXED DISODIUM

CROSS REFERNCE TO RELATED APPLICATION

This application is a 35 U.S.C. 371 National Phase Application from PCT/EP2010/06132, filed Nov. 24, 2010, which claims the benefit of U.S. Ser. No. 61/264,018 filed on Nov. 24, 2009, the disclosures of which are incorporated herein in their entirety by reference.

The present invention relates to a new polymorphic or crystalline form of Pemetrexed Disodium, processes for its preparation and its use, in particular for the preparation of medicaments.

N-[4-[2-(2-amino-4,7-dihydro-4-oxo-3H-pyrrolo[2,3-d]-pyrimidin-5-yl)ethyl]benzoyl]-L-glutamic acid or N-[4-[2-(2-amino-4,7-dihydro-4-oxo-1H-pyrrolo[2,3-d]-pyrimidin-5-yl)ethyl]benzoyl]-L-glutamic acid (also known as "Pemetrexed")

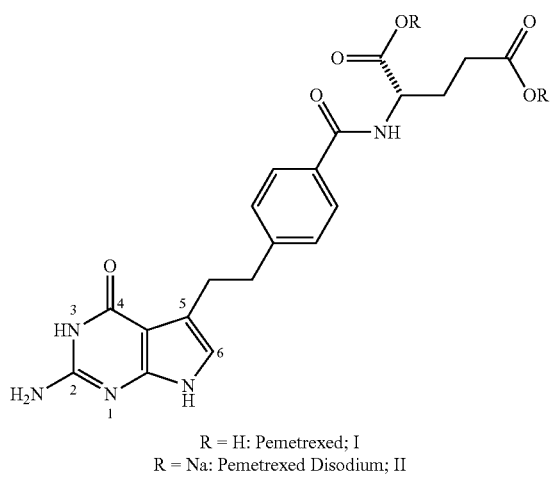

R = H: Pemetrexed; I
R = Na: Pemetrexed Disodium; II is a known compound. Pemetrexed Disodium is an known anticancer agent. It is clinically active in several solid tumors and approved for treatment of malignant pleural mesothelioma (MPM) and metastatic non-small cell lung cancer (NSCLC). Pemetrexed Disodium is supplied as a sterile lyophilized powder for intravenous administration.

The compound of formula I including pharmaceutically salts thereof as well as a process for its preparation is at first and specifically disclosed in EP patent no. 0432677 B1. The preparation and isolation of Pemetrexed (compound of formula I) as its Disodium salt (compound of formula II) was described for the first time in WO patent no. 9916742 A1 and in Drugs of the future 1998, 23(5), 498-507 as well as by Charles J. Barnett et al. in Organic Process Research & Development, 1999, 3, 184-188 and by Peter Norman in Current Opinion in Investigational Drugs 2001, 2(11), 1611-1622.

Detailed information about the crystalline form of Pemetrexed Disodium prepared according to the process as described above were not provided but it is reported by Charles J. Barnett et al. in Organic Process Research & Development, 1999, 3, 184-188 that the disodium salt II was obtained as a hygroscopic solid.

The first crystalline form of Pemetrexed Disodium has been described in WO patent no. 0114379 designated Disodium MTA Hydrate Form I (MTA=multi-targeted antifolate, disodium N-[4-[2-(2-amino-4,7-dihydro-4-oxo-3H-pyrrolo [2,3-d]-pyrimidin-5-yl)ethyl]benzoyl]-L-glutamic acid salt). The Disodium MTA Hydrate Form I obtained according to the Examples 2, 3 and 4 contained different amounts of water (Example 2: water=9.1%; Example 3: water=17.7%; Example 4: water=11.7%). The Disodium MTA Hydrate Form I has a typical XRD pattern as shown in FIG. 4 (the corresponding 2theta values have been calculated from the provided d-spacing values).

An improved crystalline form of Pemetrexed Disodium has been disclosed in WO patent no. 0162760. It is teached that Pemetrexed Disodium can exist in the form of a heptahydrate (Form II; theoretical amount of water: approx 21%) which is much more stable than the previously known 2.5 hydrate (Form I; theoretical amount of water: 8.7%). The Pemetrexed Disodium Heptahydrate Form (Form II) has a typical XRD pattern as shown in FIG. 5 (the corresponding 2theta values have been calculated from the provided d-spacing values).

The Chinese patent no. 1778802 describes a hydrate or trihydrate form of Pemetrexed Disodium. The preparation of Pemetrexed Disodium hydrate or trihydrate includes crystallization from water and water soluble solvent. An overview of the X ray powder diffraction data for Pemetrexed Disodium Hydrate provided in Chinese patent no. 1778802 is shown in FIG. 6.

The WO patent no. 2008124485 disclose besides crystalline Forms of the diacid Pemetrexed also amorphous Pemetrexed Disodium as well as a crystalline Form III thereof including a composition containing a major amount of amorphous Form And a minor amount of crystalline Form III of Pemetrexed Disodium. An overview of the X ray powder diffraction data for Pemetrexed Disodium crystalline Form 3 is shown in FIG. 7.

EP patent application no. 2072518 disclose a stable amorphous form of Pemetrexed Disodium.

Generally the ability of a given compound to exist in more than one solid form and more strictly in more than one distinct crystal structure is called polymorphism.

If not otherwise stated then the following terms and abbreviations will be used throughout the description:

The abbreviation XRPD means X-ray powder diffraction and is interchangeable with PXRD which means powder X-ray diffraction.

The term solid forms or solid state as used herein encompass crystalline or amorphous forms of a given compound.

The term amorphous form as used herein refers to a solid state of a given compound which consist of disordered arrangement of the molecules.

The term crystalline or crystalline forms as used herein encompass polymorphs, pseudopolymorphs or desolvated solvates of a given compound. It generally refers to a solid state form which consists of orderly arrangement of structural units. Thus different crystalline forms of the same compound arise from different packing of the molecules in the solid state, which results in different crystal symmetries and/or unit cell parameter.

The terms polymorph or polymorphic form as used herein refers to crystals of the same compound that differs only in the arrangement and/or conformation of the molecule in the crystal lattice but not in the composition.

The term pseudopolymorph, pseudopolymorphic form or solvate as used herein refers to a crystal form of a compound that incorporates either stoichiometric or non-stoichiometric amounts of solvent. In special case when the incorporated solvent is water then it is called a hydrate. Numeric prefixes denote the number of equivalents of the incorporated solvent (e.g. 7Hydrate=Heptahydrate=7 equivalents of water are present). Solvates without numeric prefixes are generally called monosolvates.

The term desolvated solvates as used herein refers to a crystalline form obtained by removal of the solvents from corresponding solvates e.g. by drying in vacuum, usually without significant change of the crystal structure.

It will be apparent to those skilled in the art that depending of the used physical technique, the characterization of mixed solid forms may give a composite pattern or spectrum consisting of the respective solid forms.

Different solid forms of a compound typically differ in their physical and chemical properties based on the kind of the arrangement of the molecules which also includes different arrangements of the molecules in the crystal lattice.

Therefore, a given substance may give rise to a variety of solid forms, in particular a variety of crystalline forms, wherein each form has different and distinct physical and chemical properties, such as different solubility profiles, different thermodynamic and chemical stabilities, different melting points temperatures and/or different x-ray diffraction peaks.

Different solid forms of a compound can be typically distinguished by X-ray diffraction, in particular powder x-ray diffraction (PXRD) and by other methods such as, Differential Scanning calorimetry (DSC), infrared spectroscopy, Raman spectroscopy or solid state NMR, for example.

However, as acknowledged by the person skilled in the art, the presence of new solid forms of a known chemical compound, cannot be foreseen. Neither the existence of crystalline phases nor the number of polymorphic forms can be foreseen. Also the conditions under which crystallization takes place and the characteristics of the polymorphic forms or solvates cannot be predicted.

Since properties such as the solubility and stability and consequently the suitability for use and storage of each solid form may vary, identifying the existence of different solid forms and in particular of different crystalline forms is essential for providing pharmaceuticals with increased storage stability or predicable solubility profiles. Thus, it is desirable to investigate all solid state forms of a drug, including all crystalline forms.

Accordingly, it was the object of the present invention to provide a new crystalline form of Pemetrexed Disodium, in particular a form which has a favorable property profile, preferably with respect to the use in a pharmaceutical composition.

The object was solved by providing a new crystalline form of Pemetrexed Disodium which has at least one property of
a) a water content of less than 8.0% (w/w), more preferably of less than 7.0% (w/w) and even more preferably of less than 6.0% (w/w);
b) characteristic reflexes in an X-ray powder diffractogram using $CuK_\alpha$ radiation with $CuK_\beta$ filter at a 2θ angle [°]: 7.7±0.2, 9.7±0.2, 18.6±0.2, 19.2±0.2, 20.4±0.2, 24.3±0.2, 26.6±0.2, 28.7±0.2, 28.9±0.2, 30.0±0.2,
c) characteristic signals in FT (Fourier-Transformation) Infrared spectra at 3469±2 $cm^{-1}$, 1691±2 $cm^{-1}$, 1640±2 $cm^{-1}$, 1576±2 $cm^{-1}$, 1490±2 $cm^{-1}$, 1454±2 $cm^{-1}$, 1408±2 $cm^{-1}$, 1393±2 $cm^{-1}$, 1287±2 $cm^{-1}$, 676±2 $cm^{-1}$, and/or
d) a Differential Scanning Calorimetry (DSC) diagram having no substantial endotherm peak between 110-200° C.

Herein, the crystalline form of Pemetrexed Disodium according to the invention may be named "Pemetrexed Disodium Form IV" or "Pemetrexed Disodium IV".

The characterization of crystalline compounds by X-ray powder diffraction (XPRD) is known to the person skilled in the art (c.f. e.g. European Pharamcopoeia 6.3, 2.9.33 "Characterisation of crystalline solids by XRPD" 2009).

According to a preferred embodiment the X-ray powder diffractogram as defined above (item (b)) shows further characteristic reflexes selected from the group consisting of 5.5±0.2, 10.9±0.2, 13.0±0.2, 13.6±0.2, 21.8±0.2.

According to another preferred embodiment the X-ray powder diffractogram of Pemetrexed Disodium Form IV shows at least 20, more preferably 25, more preferably 30, more preferably 35, even more preferably 40 and most preferably all of the characteristic reflexes selected from the group consisting of 5.5±0.2, 7.7±0.2, 9.2±0.2, 9.7±0.2, 10.9±0.2, 13.0±0.2, 13.6±0.2, 15.3±0.2, 16.0±0.2, 16.7±0.2, 17.0±0.2, 18.1±0.2, 18.6±0.2, 19.2±0.2, 20.0±0.2, 20.4±0.2, 21.8±0.2, 22.3±0.2, 22.7±0.2, 23.0±0.2, 24.3±0.2, 25.9±0.2, 26.6±0.2, 27.0±0.2, 27.2±0.2, 28.0±0.2, 28.7±0.2, 28.9±0.2, 30.0±0.2, 30.8±0.2, 31.5±0.2, 32.0±0.2, 33.6±0.2, 34.2±0.2, 34.6±0.2, 35.0±0.2, 36.2±0.2, 37.1±0.2, 37.9±0.2, 38.2±0.2, 38.9±0.2, 39.4±0.2.

In an especially preferred embodiment Pemetrexed Disodium Form IV is characterised by the X-ray powder diffractogram shown in FIG. 1a and/or Fig. 1b.

According to a further preferred embodiment of the invention, the FT-Infrared spectra as defined above under item (c) the FT-Infrared spectra shows further characteristic signals selected from the group consisting of 3306±2 $cm^{-1}$, 1610±2 $cm^{-1}$, 1228±2 $cm^{-1}$, 903±2 $cm^{-1}$, 778±2 $cm^{-1}$.

Preferably Pemetrexed Disodium Form IV is further characterised by a FT-Infrared spectra which shows preferably 20, more preferably 30, even more preferably 40 and most preferably all characteristic signals at selected from the group consisting of 3469±2 $cm^{-1}$, 3420±2 $cm^{-1}$, 3407±2 $cm^{-1}$, 3388±2 $cm^{-1}$, 3306±2 $cm^{-1}$, 3206±2 $cm^{-1}$, 3098±2 $cm^{-1}$, 2925±2 $cm^{-1}$, 2901±2 $cm^{-1}$, 2867±2 $cm^{-1}$, 2752±2 $cm^{-1}$, 2364±2 $cm^{-1}$, 2355±2 $cm^{-1}$, 2323±2 $cm^{-1}$, 2292±2 $cm^{-1}$, 2165±2 $cm^{-1}$, 1984±2 $cm^{-1}$, 1691±2 $cm^{-1}$, 1640±2 $cm^{-1}$, 1610±2 $cm^{-1}$, 1576±2 $cm^{-1}$, 1530±2 $cm^{-1}$, 1520±2 $cm^{-1}$, 1490±2 $cm^{-1}$, 1454±2 $cm^{-1}$, 1409±2 $cm^{-1}$, 1393±2 $cm^{-1}$, 1349±2 $cm^{-1}$, 1287±2 $cm^{-1}$, 1249±2 $cm^{-1}$, 1227±2 $cm^{-1}$, 1212±2 $cm^{-1}$, 1181±2 $cm^{-1}$, 1161±2 $cm^{-1}$, 1149±2 $cm^{-1}$, 1140±2 $cm^{-1}$, 1105±2 $cm^{-1}$, 1092±2 $cm^{-1}$, 1081±2 $cm^{-1}$, 1040±2 $cm^{-1}$, 1018±2 $cm^{-1}$, 1000±2 $cm^{-1}$, 950±2 $cm^{-1}$, 903±2 $cm^{-1}$, 876±2 $cm^{-1}$, 859±2 $cm^{-1}$, 846±2 $cm^{-1}$, 820±2 $cm^{-1}$, 778±2 $cm^{-1}$, 761±2 $cm^{-1}$, 741±2 $cm^{-1}$, 715±2 $cm^{-1}$, 706±2 $cm^{-1}$, 689±2 $cm^{-1}$, 676±2 $cm^{-1}$.

Figure 2A:
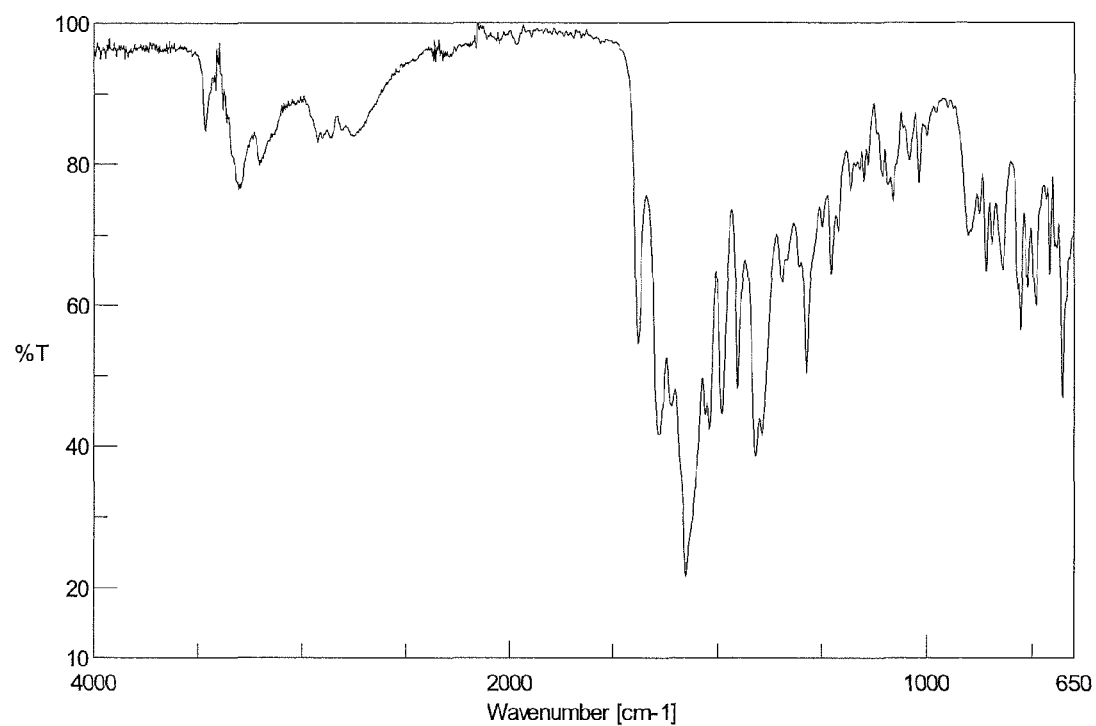

According to an especially preferred embodiment Pemetrexed Disodium Form IV is characterised by the FT-Infrared spectra shown in FIG. 2a and/or Fig. 2b.

Figure 3:
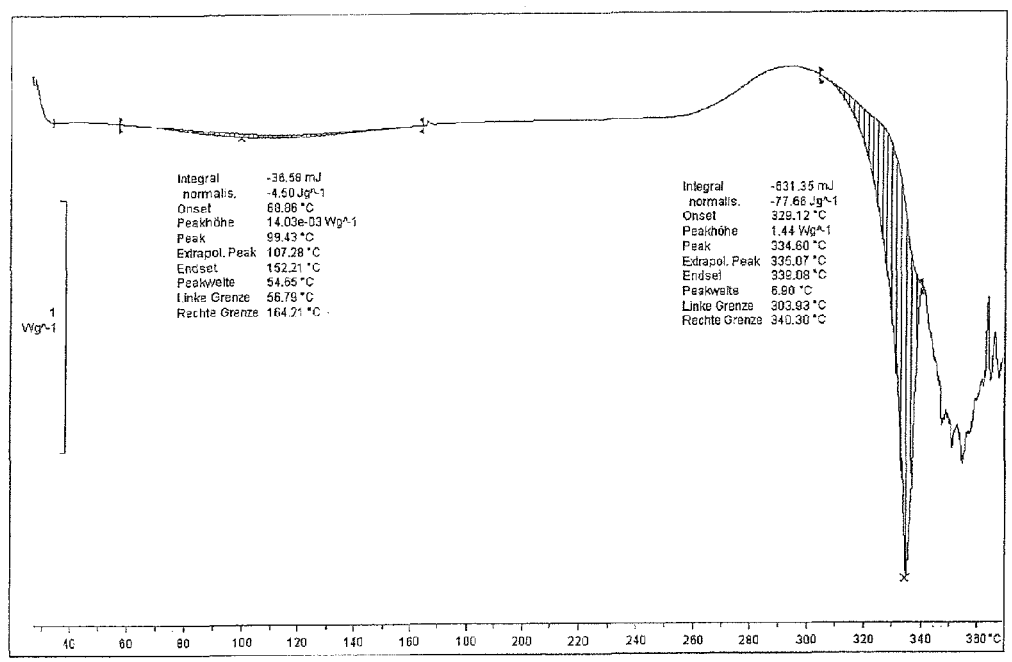

Pemetrexed Disodium Form IV may be also characterised by Differential Scanning Calorimetry (DSC). In a further preferred embodiment Pemetrexed Disodium Form IV is characterised by the DSC shown in FIG. 3.

In an especially preferred embodiment Pemetrexed Disodium Form IV is characterised by at least two properties, more preferably three properties and most preferably all four properties selected from the group consisting of PXRD, FT-IR, water-content and DSC as defined above.

Another aspect of the invention relates to a pharmaceutical composition comprising Pemetrexed Disodium Form IV together with a pharmaceutical acceptable carrier, diluent and/or excipient.

In general, such carriers, diluents and/or excipients are known to the person skilled in the art.

A diluent according to the invention is any compound which is pharmaceutical acceptable and suitable to increase the bulk volume of the pharmaceutical composition, so that the final product has the proper form and volume for administration by the patient or physician. Examples of diluents are water, vegetable fats and oils, lactose, sucrose, glucose, mannitol, sorbitol, calcium carbonate, calcium phosphate, kaolin, microcrystalline cellulose, starch etc. and combinations thereof. Especially preferred is mannitol.

Examples of excipients are antiadherents, binders (e.g. acaia gum, gelatin, cellulose, cellulose derivatives, polyvinyl pyrrolidone, sodium alginate, starch, sucrose, polyethylene glycol, etc.), buffer salts, coatings (e.g. cellulose, synthetic polymers, shellac, polysachamides etc.), disintegrants (e.g. starch, cellulose, crosslinked polyvinyl pyrrolidone, sodium starch glycolate, sodium carboxymethyl cellulose, methyl cellulose, gums such as agar, guar, etc.), flavors and colors, gliadants, lubricants (e.g. talc, silica, magnesium stearate etc.), preservatives (e.g. antioxidants like vitamin A, vitamin E, vitamin C, retinyl palmitate and selenium, methionine, cysteine, citric acid, sodium citrate, methyl paraben, propyl paraben etc.), sorbents, sweeteners, wetting agents and others including e.g. gelatin, casein, lecithin, gum acacia, cholesterol, tragacanth, stearic acid, benzalkonium chloride, calcium stearate, glycerol monostearate, cetostearyl alcohol, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecylsulfate, carboxymethylcellulose calcium, cellulose derivatives, magnesium aluminum silicate, triethanolamine, polyvinyl alcohol, polyvinylpyrrolidone etc. as well as any combination thereof.

The pharmaceutical compositions according to the invention are preferably provided and/or stored in a lyophilized form.

The pharmaceutical compositions according to the invention may be administered in any dosage form, e.g. liquid, syrup, ointment, powder, elixir, injectable solution, etc. The pharmaceutical compositions can be administered, for example, orally, parenterally, intravenously, rectally, nasally, by inhalation or topically, especially orally, intravenously or nasally, the preferred administration depending on the particular case.

Dosage forms may be adapted for administration to the patient by oral, buccal, parenteral, ophthalmic, rectal and transdermal routes. Oral dosage forms include, but are not limited to, tablets, pills, hard or soft capsules, suspensions, powders, lozenges, elixirs and the like.

Actual dosage levels of the pharmaceutical composition of the invention may be varied to obtain an amount of Pemetrexed Disodium Form IV that is effective to obtain a desired therapeutic response for a particular composition and a method of administration for treatment of a subject, preferably a mammal, more preferably a human. The selected dosage level depends upon such factors as, for example, the desired therapeutic effect, the route of administration, the desired duration of treatment, and other factors.

The total daily dose of the polymorph form of Pemetrexed Disodium Form IV according to the invention may be administered to a patient in single or divided dose and can vary widely depending upon a variety of factors including, for example, the body weight, general health, gender, diet, time and route of administration, rates of absorption and excretion, combination with other drugs, the severity of the particular condition being treated, etc.

According to a further embodiment the pharmaceutical composition of the invention is for modulation, preferably inhibition, of the folate metabolic pathway including thymidylate synthase (TS), dihydrofolate reductase (DHFR) and/or glycinamide ribonucleotide formyl transferase (GRAFT). In an especially preferred embodiment the pharmaceutical composition of the invention is for the treatment and/or prophylaxis of cancer, in particular solid tumors, which are preferably selected from the group consisting of malignant pleural mesothelioma (MPM) and metastatic non-small cell lung cancer (NSCLC).

According to a further embodiment, the pharmaceutical composition of the invention may comprise a further active agent, such as (i) antimetabolites, such as cytarabine, fludarabine, 5-fluoro-2'-deoxyuiridine, gemcitabine, hydroxyurea or methotrexate; (ii) DNA-fragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cycloheximide, puromycin or diphteria toxin; (vi) topoisomerase I poisons, such as camptothecin or topotecan; (vii) topoisomerase II poisons, such as etoposide (VP-16) or teniposide; (viii) microtubule-directed agents, such as colcemid, colchicine, paclitaxel, vinblastine or vincristine; (ix) kinase inhibitors such as flavopiridol, or staurosporin; (x) miscellaneous investigational agents such as thioplatin, phenylbutyrate, or farnesyl transferase inhibitors; polyphenols such as quercetin, resveratrol, piceatannol, epigallocatechine gallate, theaflavins, flavanols, procyanidins, betulinic acid and derivatives thereof; (xi) hormones such as glucocorticoids or fenretinide; (xii) hormone antagonists, such as tamoxifen, finasteride or LHRH antagonists.

Another aspect of the invention relates to the use of Pemetrexed Disodium Form IV for the manufacture of a medicament for modulating, preferably inhibiting, the folate metabolic pathway including thymidylate synthase, dihydrofolate reductase and/or glycinamide ribonucleotide formyl transferase. Especially preferred is the manufacture of medicament for the treatment and/or prophylaxis of cancer, in particular solid tumors, which are preferably selected from the group consisting of malignant pleural mesothelioma and metastatic non-small cell lung cancer.

A further aspect of the invention relates to a or the preparation of Pemetrexed Disodium Form IV comprising the steps
  (a) providing a mixture of Pemetrexed Disodium in a solvent, preferably C1-C4 alcohols, more preferably EtOH, comprising preferably 0% to 5% $H_2O$ (v/v), even more preferably 1% to 4% $H_2O$ (v/v), and most preferably 1% to 3% $H_2O$ (v/v),
  (b) addition of seeding crystals,
  (c) heating under reflux and optionally adding NaOH until transformation to Pemetrexed Disodium according to any of the claims 1-9 is complete, and
  (d) isolation of the product, preferably by filtration, more preferably hot filtration or
(a') providing Pemetrexed Monosodium in a solvent, preferably C1-C4 alcohols, more preferably EtOH, comprising 0% to 5% $H_2O$ (v/v), even more preferably 1% to 4% $H_2O$ (v/v), and most preferably 1% to 3% $H_2O$ (v/v), (b') slow or portionwise addition of about 0.5 to 1.5 mole equivalents of NaOH, preferably 0.7 to 1.3 mole equivalents, even more preferably 0.8 to 1.1 mole equivalents, and most preferably 1.0 equivalents, (c') heating under reflux and optionally adding NaOH until transformation to Pemetrexed Disodium according to any of the claims 1-9 is complete, and (d') isolation of the product, preferably by filtration, more preferably hot filtration or (a'') providing Pemetrexed in a solvent, preferably C1-C4 alcohols, more preferably EtOH comprising 0% to 5% $H_2O$ (v/v), even more preferably 1% to 4% $H_2O$ (v/v), and most preferably 1% to 3% $H_2O$ (v/v), (b'') slow or portionwise addition of about 1.0 to 3.0 mole equivalents of NaOH, preferably 1.7 to 2.3 mole equivalents, even more preferably 1.8 to 2.1 mole equivalents, and most preferably 2.0 equivalents, (c'') heating under reflux and optionally adding NaOH until transformation to Pemetrexed Disodium according to any of the claims 1-9 is complete, and (d'') isolation of the product, preferably by filtration, more preferably hot filtration.

"Slow" in terms of the present application is to be to understand be the person skilled in art and depends on the batch size. However, generally, it means over a period of hours, not minutes.

According to a preferred embodiment the seed crystals of step (b) are of Pemetrexed Monosodium, preferably in an amount of about 5 to 30 mol %, even more preferably 10 to 20 mol %, and most preferably 15 mol %.

FIGURES

Figure 18A:
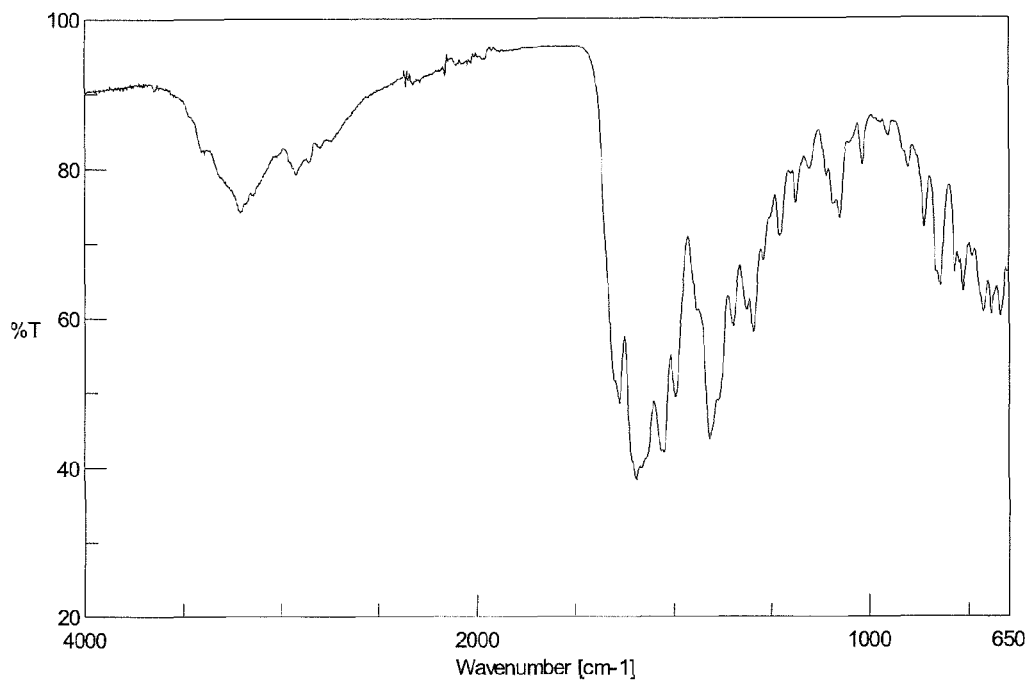
Figure 19:
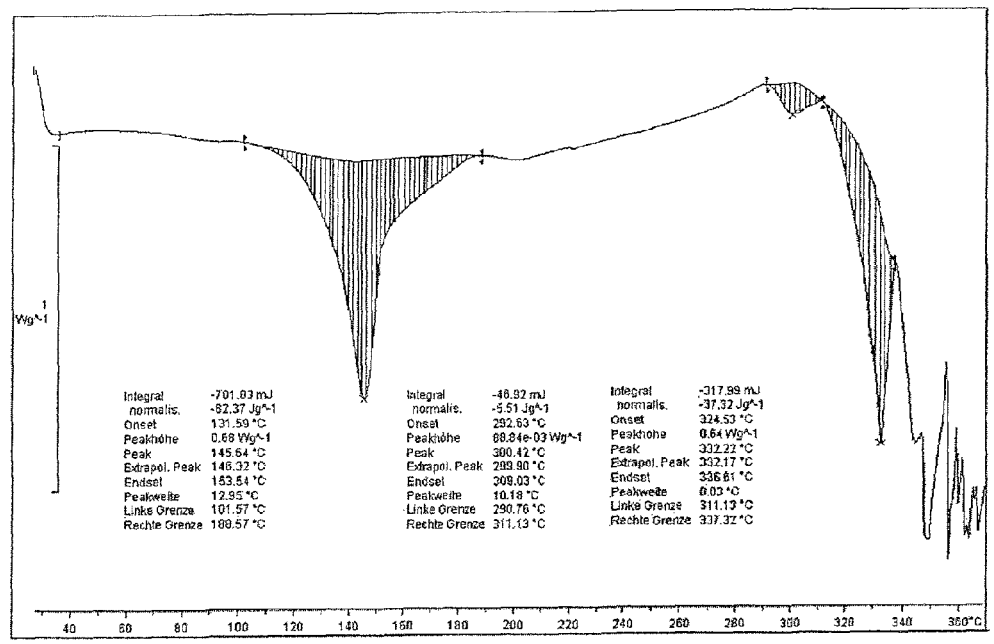

FIG. 1: 1a: PXRD-profile of Pemetrexed Disodium Form IV
1b: PXRD-data of Pemetrexed Disodium Form IV
FIG. 2: 2a: FT-IR-spectra of Pemetrexed Disodium Form IV
2b: FT-IR-data of Pemetrexed Disodium Form IV
FIG. 3: DSC of Pemetrexed Disodium Form IV
FIG. 4: PXRD peak listing of Disodium MTA Hydrate Form I as described in WO patent application no. 0114379 (2theta values have been calculated from d-spacing values based on Cu wave length λ=1.54056 Å)
FIG. 5: PXRD peak listing of Pemetrexed Disodium 7 Hydrate described in WO patent no. 01/62760 (2theta values have been calculated from d-spacing values based on Cu wave length λ=1.54056 Å)
FIG. 6: PXRD peak listing of Pemetrexed Disodium Hydrate described in CN patent no. 1778802 (2theta values have been calculated from d-spacing values based on Cu wave length λ=1.54056 Å)
FIG. 7: PXRD peak listing of Pemetrexed Disodium Form III described in WO patent no. 2008124485
FIG. 8: 8a: PXRD-profile of Pemetrexed Disodium Heptahydrate (form II)
8b: PXRD data of Pemetrexed Disodium Heptahydrate
FIG. 9: 9a: FT-IR-profile of Pemetrexed Disodium Heptahydrate
9b: FT-IR data of Pemetrexed Disodium Heptahydrate
FIG. 10: DSC-profile of Pemetrexed Disodium Heptahydrate
FIG. 11: 11a: PXRD-profile of Pemetrexed Disodium 2,5 hydrate (form I)
11b: PXRD data of Pemetrexed Disodium 2,5 hydrate
FIG. 12: 12a: FT-IR-profile of Pemetrexed Disodium 2,5 hydrate
12b: FT-IR data of Pemetrexed Disodium 2,5 hydrate
FIG. 13: DSC-profile of Pemetrexed Disodium 2,5 hydrate
FIG. 14: PXRD-profile of Pemetrexed Disodium Form A (amorphous)
FIG. 15: 15a: FT-IR-profile of Pemetrexed Disodium Form A
15b: FT-IR data of Pemetrexed Disodium Form A
FIG. 16: DSC-profile of Pemetrexed Disodium Form A
FIG. 17: 17a: PXRD-profile of Pemetrexed Disodium Form III
17b: PXRD data of Pemetrexed Disodium Form III
FIG. 18: 18a: FT-IR-profile of Pemetrexed Disodium Form III
18b: FT-IR data of Pemetrexed Disodium Form III
FIG. 19: DSC-profile of Pemetrexed Disodium Form III
FIG. 20: Possible routes for the conversion of Pemetrexed IM8 to Pemetrexed Disodium Form IV

EXAMPLES

Solid Forms of Pemetrexed Disodium and Detailed Characterization Thereof

As described above, five solid forms of Pemetrexed Disodium have been described in the literature (Form I, Form II, Form III, "trihydrate" and an amorphous form). Except for the "trihydrate" Form, the procedures given were reproduced to obtain representative samples of the different forms including a complete characterization of that forms. In the context of this disclosure these compounds have been prepared as described in literature.

In addition to these known forms we have found a novel form, Pemetrexed Disodium Form IV, during crystallization experiments.

Pemetrexed Disodium Heptahydrate (Form II)

Figure 8A:
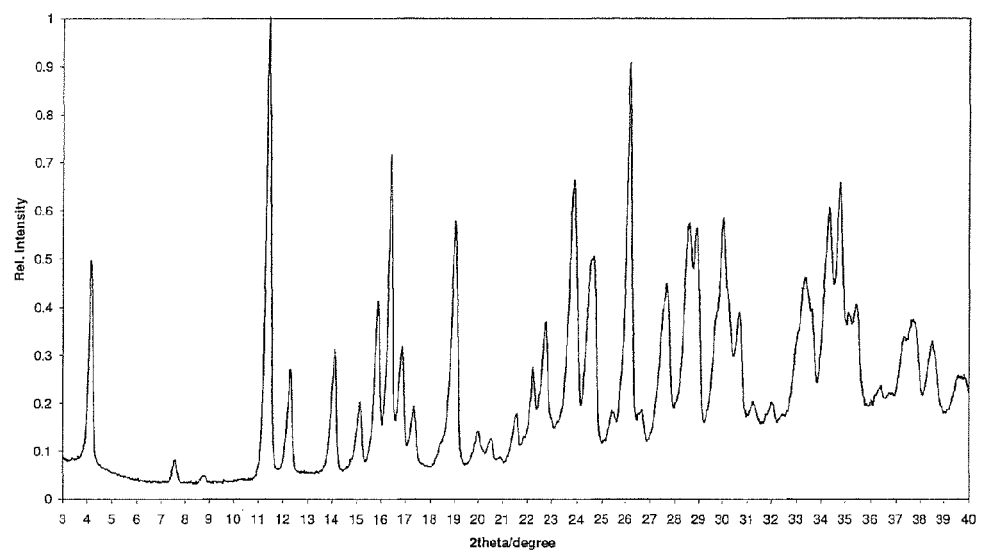
Figure 9A:
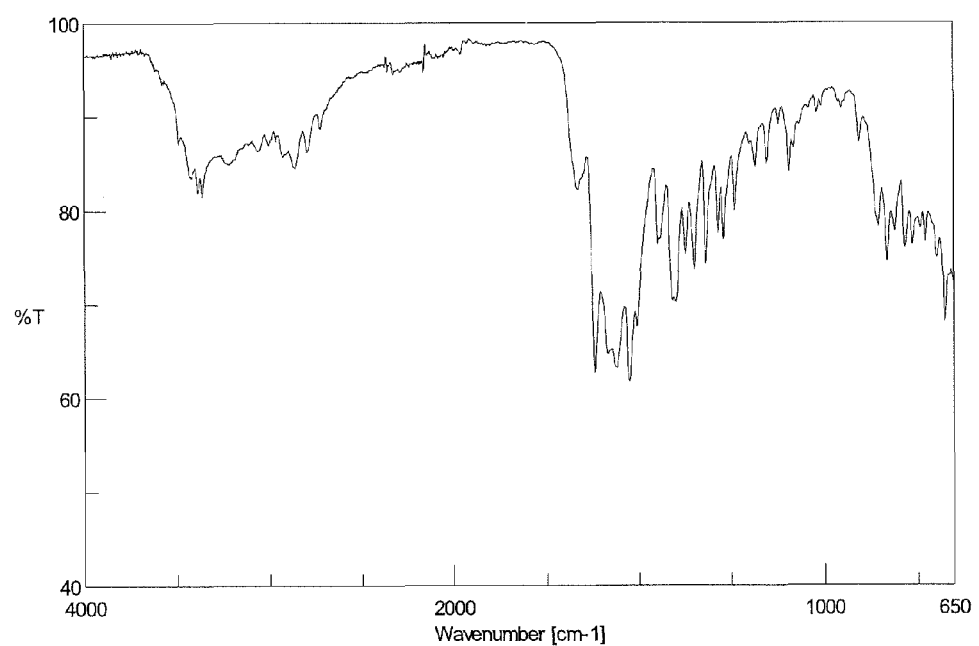
Figure 10:
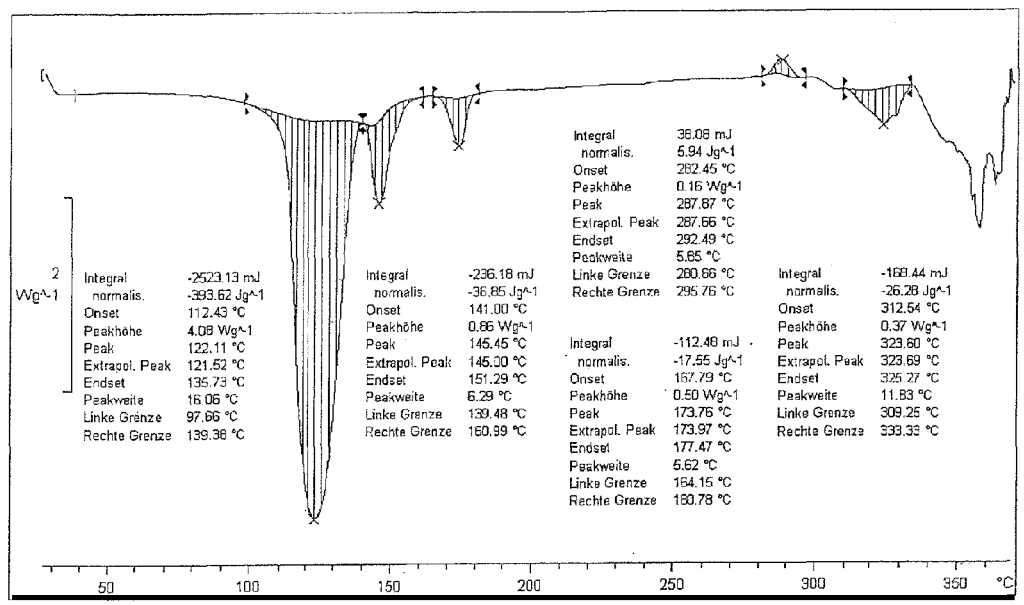

Pemetrexed Disodium Heptahydrate (Form II) is characterized by a water content of 21.1%, a sodium content of 7.7% and PXRD, IR and DSC data shown in FIGS. 8-10.

Pemetrexed Disodium 2.5 Hydrate (Form I)

Figure 11A:
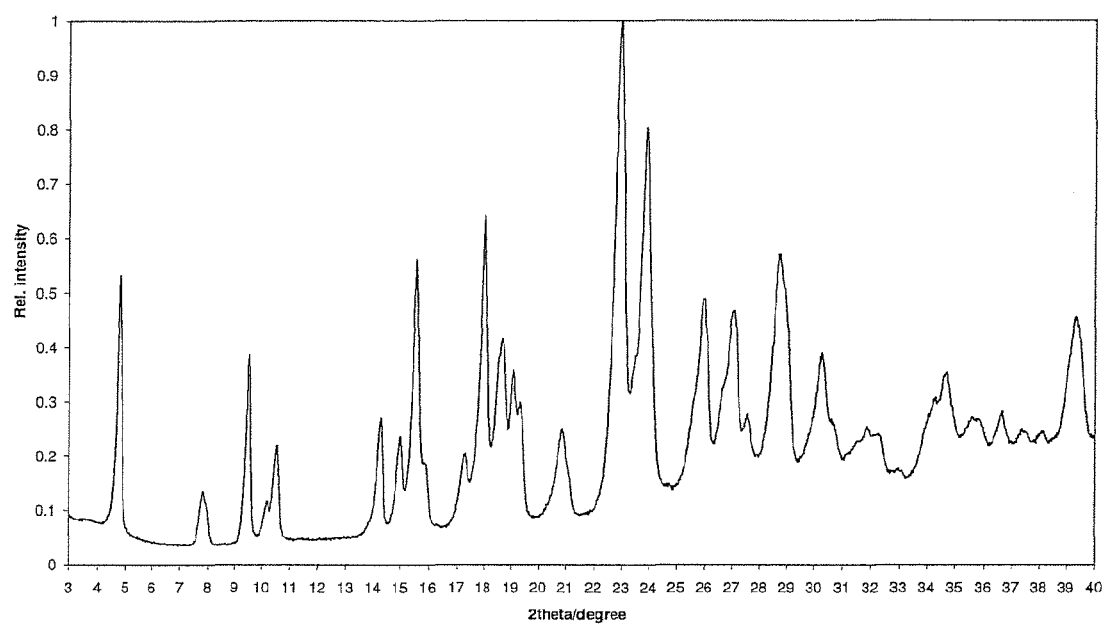
Figure 12A:
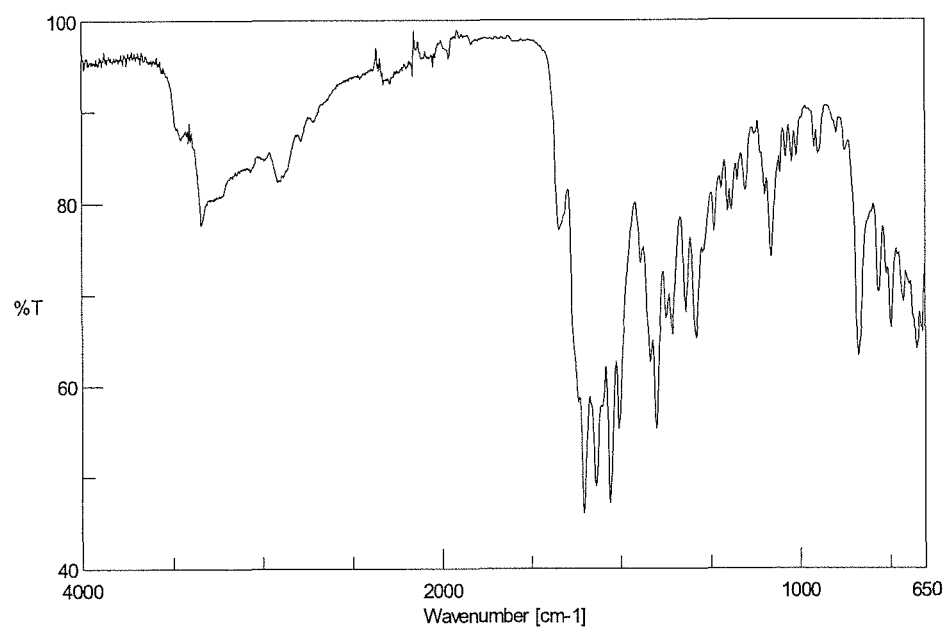
Figure 13:
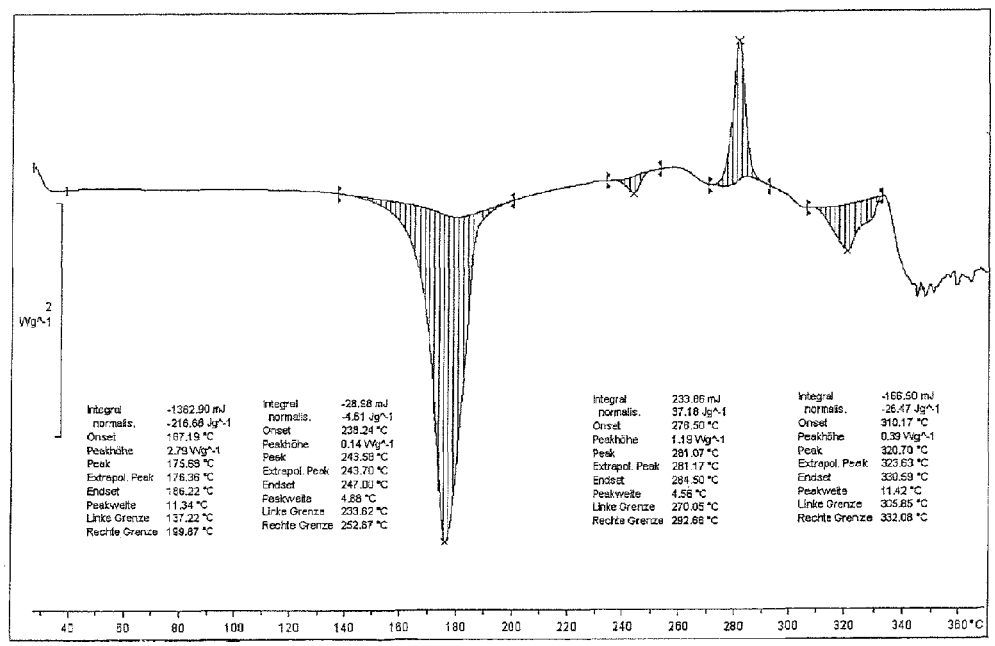

Pemetrexed Disodium 2.5 hydrate (Form I) is characterized by a water content of 8.7%, a sodium content of 8.9% and by the PXRD, IR and DSC data shown in FIGS. 11-13.

Pemetrexed Disodium Form A (Amorphous)

Figure 14:
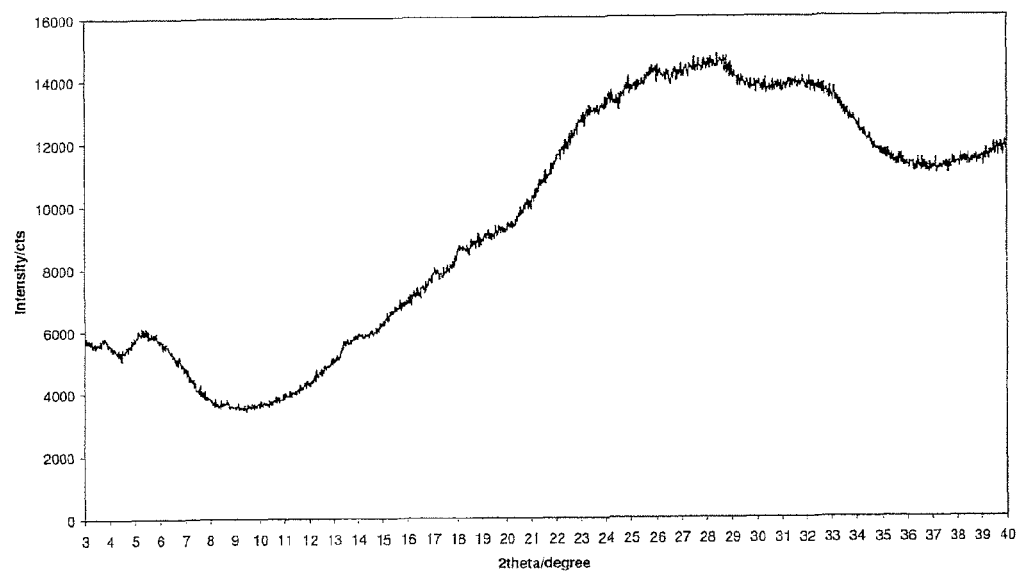
Figure 15A:
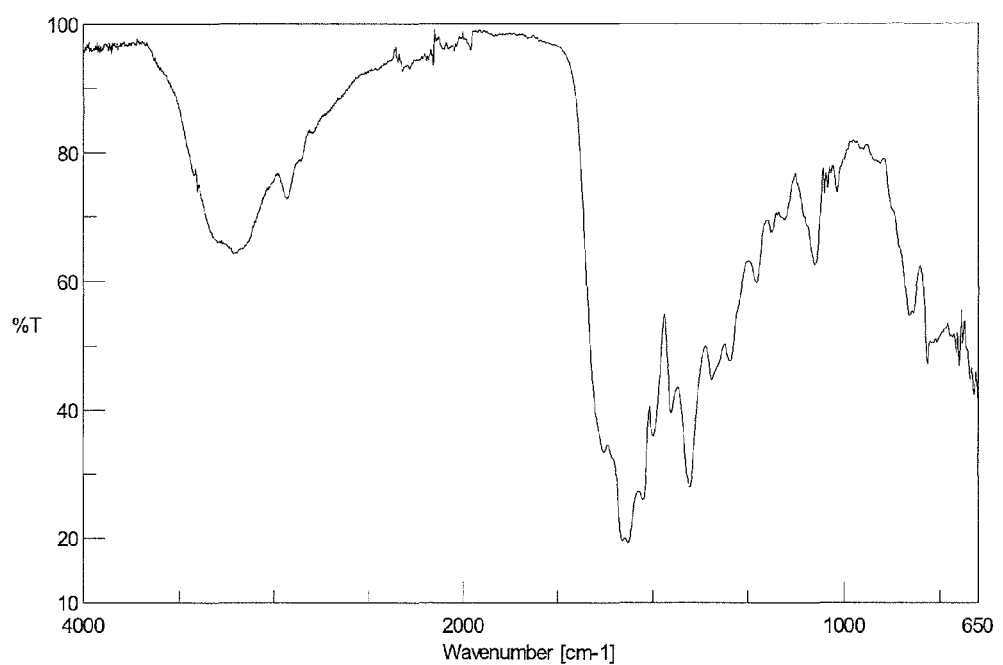
Figure 16:
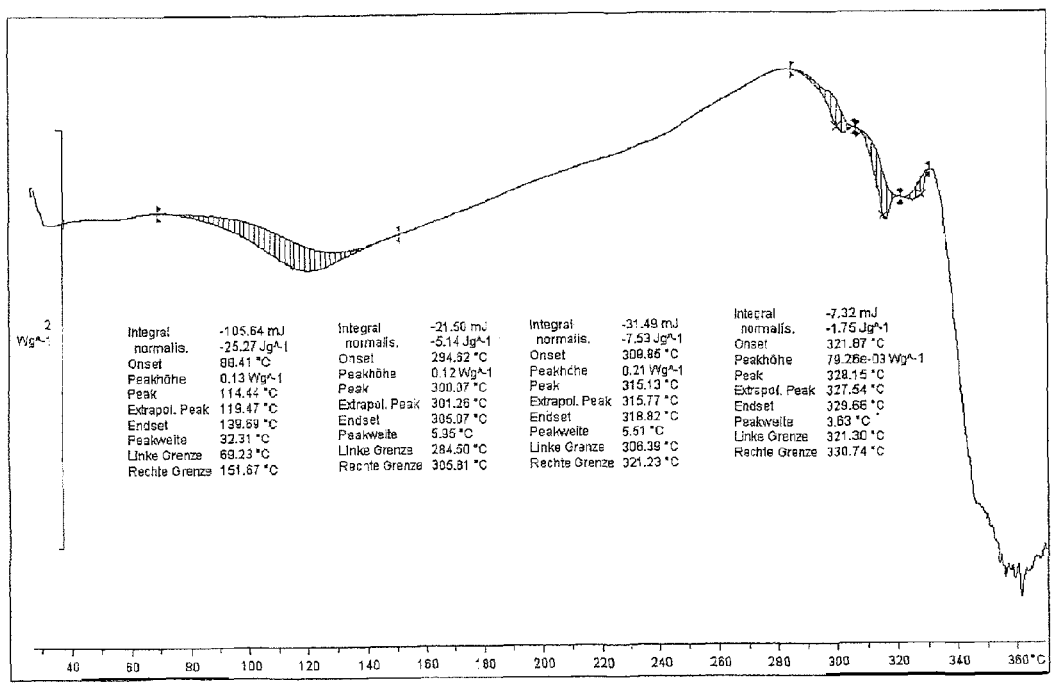

Pemetrexed Disodium Form A is an amorphous form which is characterized by a sodium content of 9.8%, FT-IR and DSC data (FIGS. 15 and 16). PXRD measurements do not show any significant crystalline part (FIG. 14).

Pemetrexed Disodium Form III

Pemetrexed Disodium Form III is described in WO patent no. 2008124485 as a mixture obtained together with Pemetrexed Disodium Form A (amorphous). By using a crystallization measurement different from the one described in WO patent no. 2008124485 a more crystalline Pemetrexed Disodium Form III was obtained. Comparison of PXRD data confirms the crystalline part of this molecule to be Pemetrexed Disodium Form III. Pemetrexed Disodium Form III is characterized by the PXRD, IR and DSC data of FIGS. 17-19.

Synthetic Route for the Preparation of Pemetrexed Disodium

Starting from commercially available materials a novel synthetic route for the synthesis of Pemetrexed-IM8 (the dimethyl ester of Pemetrexed) was developed which was then used for the preparation of Pemetrexed Disodium (Scheme 1).

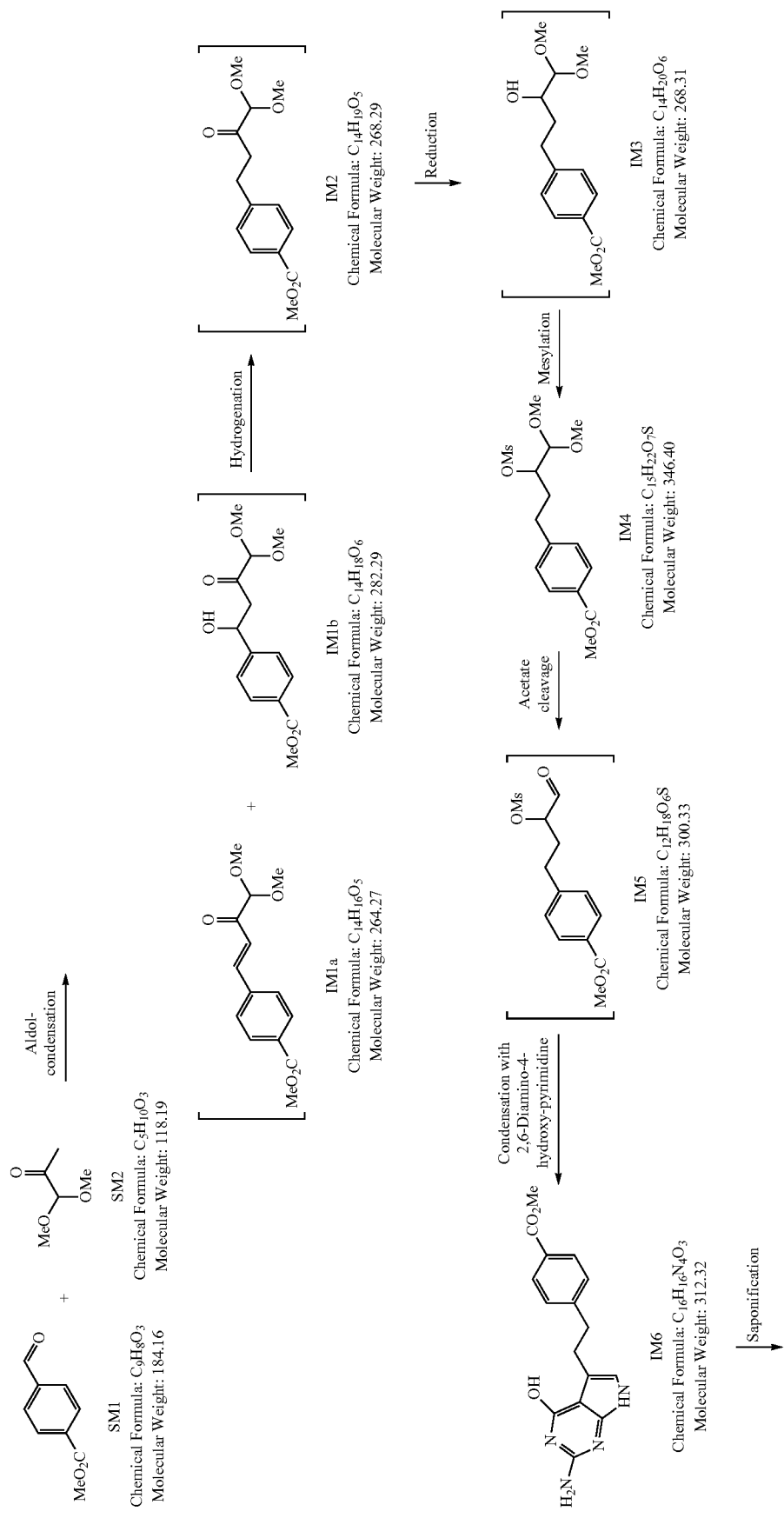

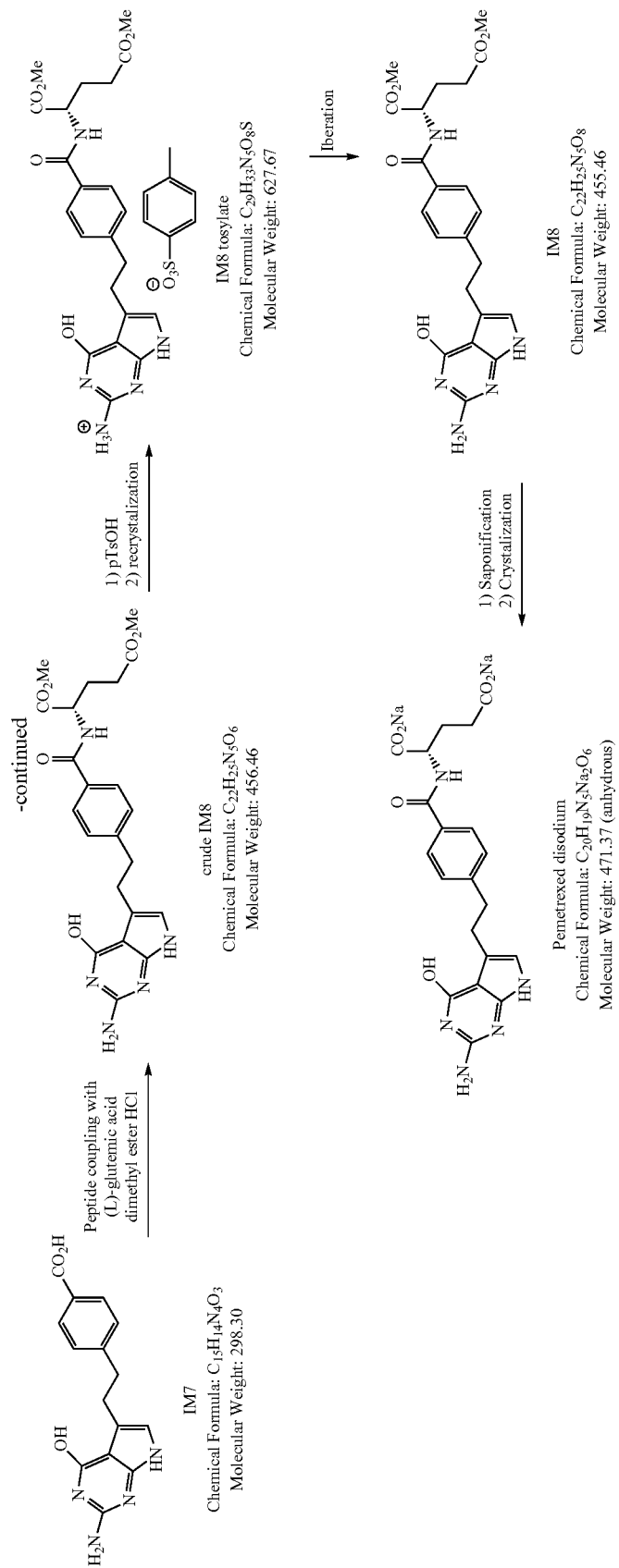

The current synthetic route for the preparation of Pemetrexed IM8 starts with an aldol-condensation reaction of Methyl-4-formylbenzoate (SM1) with 1,1-Dimethoxyacetone (SM2) to give Pemetrexed IM1a. As Pemetrexed IM1a irreversibly converts to its aldol-addition product Pemetrexed IM1b under reaction conditions the reaction mixture is directly submitted to hydrogenation (i.e. without isolation of Pemetrexed IM1a) over Pd/C to give Pemetrexed IM2. As under the hydrogenation conditions not only the double-bond of IM1a is hydrogenated but also some amount of Pemetrexed IM2 is converted to Pemetrexed IM3 (hydrogenation of the carbonyl function to the corresponding secondary alcohol) a solution of NaBH4 is added to the reaction mixture to ensure complete conversion to Pemetrexed IM3. The Pd-catalyst is removed by filtration and the reaction mixture is extracted with toluene. The combined organic layers are evaporated to give crude Pemetrexed IM3 as oil. This oil is dissolved in THF and the alcohol functionality is converted to a mesylate using MsCl and NEt3. The salts are removed by filtration, glacial acetic acid is added and THF is removed by distillation. Upon addition of water Pemetrexed IM4 crystallizes and is isolated by filtration. The dried Pemetrexed IM4 is dissolved in glacial acetic acid and gaseous HCl is added to cleave the dimethoxy acetale and liberate the aldehyde functionality of Pemetrexed IM5. Upon complete deprotection a solution of 2,6-diamino-4-hydroxypyrimidine in aq. NaOH and acetonitrile is added. Upon complete conversion the crystallized Pemetrexed IM6 is isolated by filtration. The saponification of the methyl ester of Pemetrexed IM6 to Pemetrexed IM7 is done using aqueous NaOH. Upon addition of aq. HCl first the Na-salt of Pemetrexed IM7 crystallizes from the reaction mixture. The salt is isolated by filtration, purified by slurry in a mixture of MeOH and water and then converted to Pemetrexed IM7 by pH adjustment in water using aq. HCl. Dried Pemetrexed IM7 (water content not more than 6.0%) is dissolved in DMF, activated using 1,1-carbonyldiimidazolide (CDI) and then reacted with dimethyl-L-glutamate hydrochlorid to give, upon addition of water and filtration, crude Pemetrexed IM8. This intermediate is purified by tosylate salt formation, followed by recrystallization and liberation to give pure Pemetrexed IM8. Starting with the saponification of Pemetrexed IM8 the preparation of different solid forms of Pemetrexed Disodium can be achieved.

Figure 20:
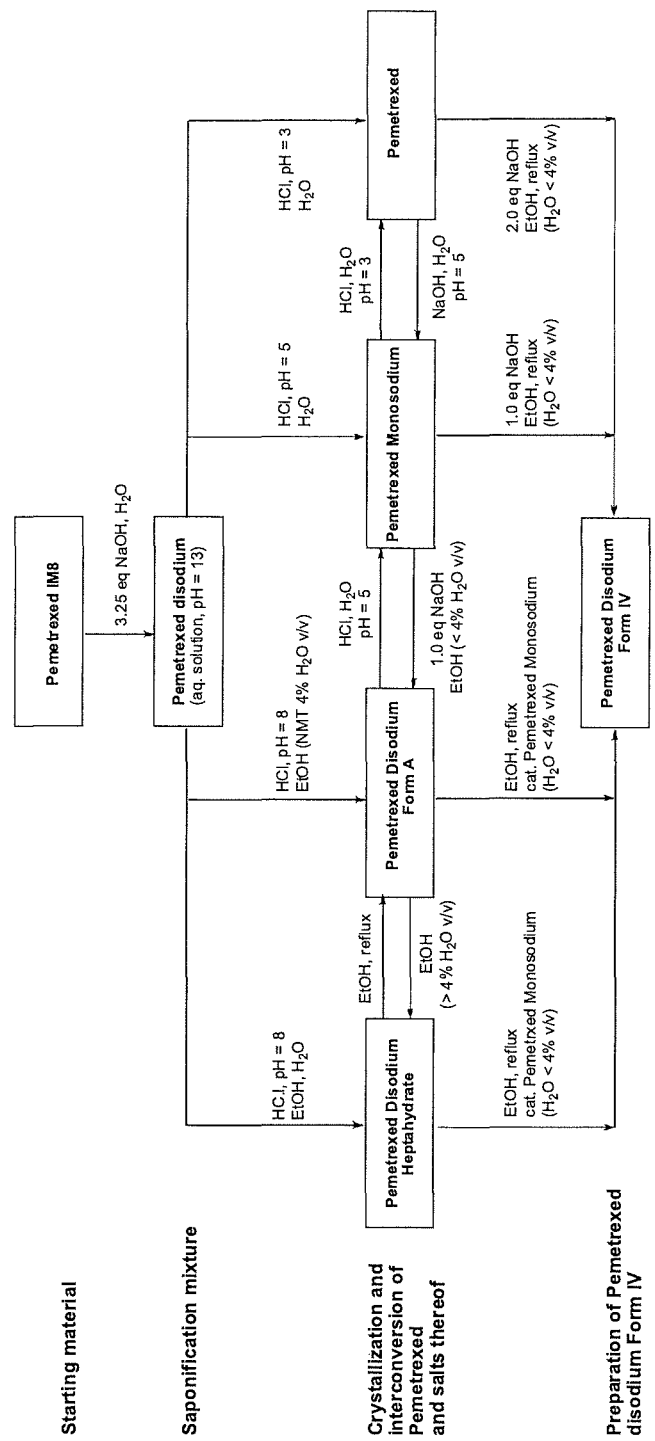

Methods For Preparing Pemetrexed Disodium Form IV and Investigation of its Stability An overview on the possible transformations of Pemetrexed IM8 to Pemetrexed Disodium Form IV is shown in FIG. 20.

Description of Possible Routes for the Preparation of Pemetrexed Disodium Form IV Starting from Pemetrexed IM8

All routes start with saponification of Pemetrexed IM8 in water at IT=20° C. to 30° C. using 3.25 eq of NaOH. Upon complete conversion an aqueous solution of Pemetrexed Disodium with a pH of 13.0 to 13.5 is obtained. Starting from this mixture the desired route can be accessed by addition of HCl to adjust the pH to a certain value (depending on the route, FIG. 20).

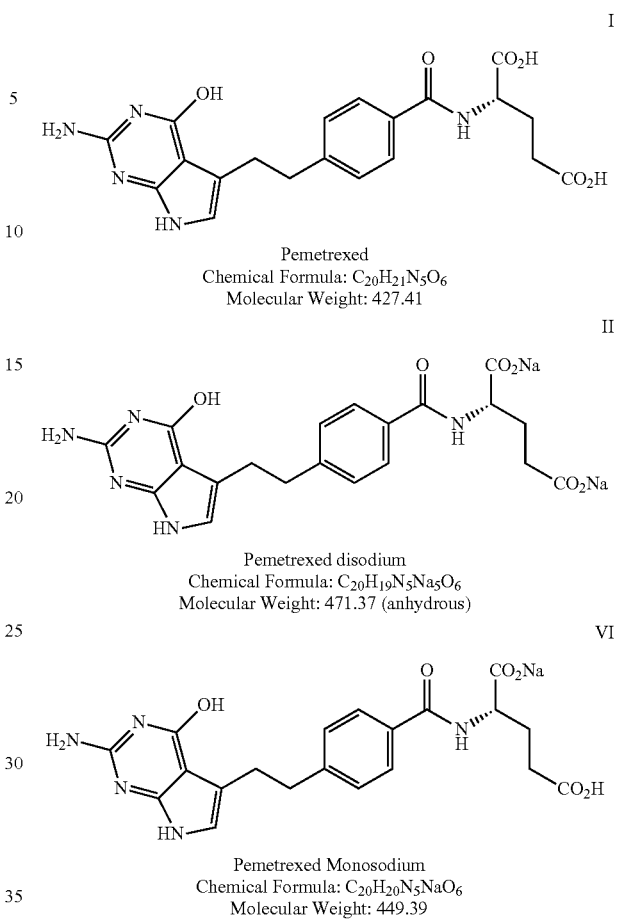

Pemetrexed
Chemical Formula: $C_{20}H_{21}N_5O_6$
Molecular Weight: 427.41

Pemetrexed disodium
Chemical Formula: $C_{20}H_{19}N_5Na_5O_6$
Molecular Weight: 471.37 (anhydrous)

Pemetrexed Monosodium
Chemical Formula: $C_{20}H_{20}N_5NaO_6$
Molecular Weight: 449.39

Structures of Pemetrexed (Compound I), Pemetrexed Disodium (Compound II) and Pemetrexed Monosodium (Compound IV)

Surprisingly we found that the crucial feature of all successful transformations to Pemetrexed Disodium Form IV is the presence of Pemetrexed Monosodium during the transformation. Routes starting from pure Pemetrexed Disodium Heptahydrate, Pemetrexed Disodium 2.5 hydrate or Pemetrexed Disodium Form A in the presence of seeding crystals of Pemetrexed Disodium Form IV were not successful and resulted in isolation of Pemetrexed Disodium Form A. The same transformations, if carried out in the presence of 0.15 eq of Pemetrexed Monosodium were successful and after addition of 0.15 eq NaOH allowed the isolation of pure Pemetrexed Disodium Form IV. The use of 0.15 eq HCl instead of 0.15 eq Pemetrexed Monosodium under the same conditions resulted in isolation of Pemetrexed Disodium Form A without any Pemetrexed Disodium Form IV. Transformations via isolated Pemetrexed Monosodium gave complete transformation to Pemetrexed Disodium Form IV if either 1.0 eq NaOH were added slowly (over a period of several hours) to Pemetrexed Monosodium or if initially only 0.85 eq of NaOH (based on Pemetrexed Monosodium) were added, followed by 0.15 eq once the transformation to Pemetrexed Disodium Form IV was complete. Very fast addition (<1 min) of 1.0 eq NaOH resulted in formation of Pemetrexed Disodium Form A containing traces of Pemetrexed Disodium Heptahydrate.

Starting from Pemetrexed (compound I) the transformation to Pemetrexed Disodium Form IV would be possible if initially 1.85 eq of NaOH were added followed by 0.15 eq once the transformation was complete. Alternatively, 2.0 eq of NaOH could be added over a long period of time (i.e several hours) to achieve formation of Pemetrexed Form IV. Fast addition (<1 min) of 2.0 eq of NaOH is assumed to result in formation of Pemetrexed Disodium Form A. All these experiments show the presence of Pemetrexed Monosodium to be crucial during the transformations. This presence can be achieved by either addition of catalytic amounts of Pemetrexed Monosodium to Pemetrexed Disodium, by slow addition over several hours of NaOH to Pemetrexed Monosodium or by portionwise addition of NaOH to Pemetrexed Monosodium. Addition of catalytic amounts of HCl to Pemetrexed Disodium (in situ preparation of Pemetrexed Monosodium) failed to give Pemetrexed Disodium Form IV.

Fast addition of NaOH to Pemetrexed Monosodium results in fast formation of Pemetrexed Disodium, thereby lacking the necessary catalytic amounts of Pemetrexed Monosodium to catalyze the transformation to Pemetrexed Disodium Form IV. EtOH as solvent and water content of EtOH were found to be crucial parameters for the transformation to Pemetrexed Disodium Form IV. So far the transformation has only been observed in EtOH containing 0-4% water (v/v). A water content>4% (v/v) results in formation of Pemetrexed Disodium Heptahydrate. Under the conditions used (EtOH containing 0-4% water (v/v)) both Pemetrexed Disodium Heptahydrate and Pemetrexed Disodium 2.5 hydrate are transformed to Pemetrexed Form A. Therefore the mechanism of the transformation to Pemetrexed Disodium Form IV is assumed to proceed via Pemetrexed Disodium Form A with Pemetrexed Monosodium acting as catalyst for the transformation.

Preparation of Pemetrexed Disodium Heptahydrate
a) Preparation of Pemetrexed Disodium Heptahydrate Starting from Pemetrexed IM8

Pemetrexed Disodium Heptahydrate was prepared by adjustment of the pH of the Pemetrexed Disodium solution after saponification from pH=13 to pH=8 using HCl followed by addition of EtOH (3 times the volume of water) to achieve crystallization. Precipitated Pemetrexed Disodium Heptahydrate was isolated by filtration, washed with a mixture of EtOH and water (4:1 v/v) followed by EtOH. The wet product was dried in vacuo at 200 mbar at 20° C. to 30° C. until water content of the dried product was 20.1% to 22.1%.
b) Conversion of Pemetrexed Disodium Form A to Pemetrexed Disodium Heptahydrate To a suspension of Pemetrexed Disodium Form A in EtOH was added water until a mixture of EtOH containing 25% water (v/v) was obtained. The resulting suspension was stirred at 20° C. to 30° C. until conversion was complete according to PXRD. Pemetrexed Disodium Heptahydrate was isolated by filtration, washed with EtOH and dried in vacuo at 200 mbar at 20° C. to 30° C. until water content of the dried product was 20.1% to 22.1%.

Preparation of Pemetrexed Disodium Form A
a) Preparation of Pemetrexed Disodium Form A Starting from Pemetrexed IM8 pH of the solution of Pemetrexed Disodium after saponification was adjusted from pH=13 to pH=8 at IT=20° C. to 30° C. using HCl. The solution was warmed to IT=50° C. and was added to a sufficient amount of EtOH at reflux so that the amount of EtOH after complete addition had a water content 4% v/v. Upon complete addition the resulting suspension was cooled to 20° C. to 30° C. and the precipitate was isolated by filtration, washed with EtOH and dried in vacuo at 50° C. at 5 mbar to give Pemetrexed Disodium Form IV.

b) Conversion of Pemetrexed Disodium Heptahydrate to Pemetrexed Disodium Form A

A suspension of Pemetrexed Disodium Heptahydrate in EtOH was stirred at IT=20° C. to 78° C. until PXRD showed complete conversion to Pemetrexed Disodium Form A. The wet product was isolated by filtration, washed with EtOH and dried in vacuo at IT=50° C. at 5 mbar to constant weight.
c) Conversion Pemetrexed Monosodium to Pemetrexed Disodium Form A To a suspension of Pemetrexed Monosodium in EtOH at 20° C. to 30° C. were added 1.0 eq of aq. NaOH (30% w/w). The resulting mixture was stirred at 20° C. to 30° C. until PXRD showed complete conversion to Pemetrexed Disodium Form A. The suspension was filtered, the wet product was washed with EtOH and dried to constant weight in vacuo at 50° C. at 5 mbar.

Preparation of Pemetrexed Monosodium
a) Preparation of Pemetrexed Monosodium Starting from Pemetrexed IM8 pH of the solution of Pemetrexed Disodium after saponification was adjusted from pH=13 to pH=8 at IT=20° C. to 30° C. using HCl. The solution was warmed to IT=50° C. and exactly 1.0 eq of aq. HCl were added. To the resulting suspension were added 10 eq. NaCl as solid and the mixture was cooled to 20° C. to 30° C. before filtration. The wet product was isolated by filtration, washed with aq. NaCl solution (10% w/w) followed by aq. EtOH (5% water v/v) and EtOH. The wet Pemetrexed Monosodium was dried in vacuo to constant weight.
b) Conversion of Pemetrexed Disodium Form A to Pemetrexed Monosodium Pemetrexed Disodium Form A was dissolved in water and the resulting solution was warmed to 50° C. before addition of 1.0 eq HCl (32% w/w). To the resulting suspension were added 10 eq NaCl as solid followed by cooling to 20° C. to 30° C. The wet product was isolated by filtration, washed with aq. NaCl solution (10% w/w) followed by aq. EtOH (5% water v/v) and EtOH. The wet Pemetrexed Monosodium was dried in vacuo at 50° C. at 5 mbar to constant weight.
c) Conversion of Pemetrexed to Pemetrexed Monosodium A suspension of Pemetrexed in water was warmed to 50° C. before addition of 1.0 eq HCl (32% w/w). To the resulting suspension were added 10 eq NaCl as solid followed by cooling to 20° C. to 30° C. The wet product was isolated by filtration, washed with aq. NaCl solution (10% w/w) followed by EtOH (5% water v/v) and EtOH. The wet Pemetrexed Monosodium was dried in vacuo at 5 mbar at 50° C. to constant weight.

Preparation of Pemetrexed
a) Preparation of Pemetrexed Starting from Pemetrexed IM8 pH of the solution of Pemetrexed Disodium after saponification was adjusted from pH=13 to pH=8 at 20° C. to 30° C. using HCl. The resulting solution was warmed to 50° C. to 60° C. and pH was further adjusted to pH≤3.0 using HCl. The resulting suspension of Pemetrexed was filtered, the wet product was washed water and dried to constant weight.
b) Conversion of Pemetrexed Monosodium to Pemetrexed The pH of a suspension of Pemetrexed Monosodium in water was adjusted to pH≤3.0 at 50° C. using HCl. The resulting suspension of Pemetrexed was filtered, the wet product was washed with water and dried to constant weight.

Preparation of Pemetrexed Disodium Form IV
a) Attempted Conversion of Pemetrexed Disodium Heptahydrate to Pemetrexed Disodium Form IV in the Presence of Seeding Crystals of Pemetrexed Disodium Form IV A suspension of Pemetrexed Disodium Heptahydrate in EtOH containing seeding crystals of Pemetrexed Disodium Form IV and 0% to 2% water (v/v) was heated to reflux for 16 h. The suspension was cooled to 20° C. to 30° C. followed by filtration. The wet product was washed with EtOH and dried in vacuo at 5 mbar at 50° C. to constant weight to give Pemetrexed Disodium Form A.

b) Conversion of Pemetrexed Disodium Heptahydrate to Pemetrexed Disodium Form IV in the Presence of Catalytic Amounts of Pemetrexed Monosodium A suspension of Pemetrexed Disodium Heptahydrate in EtOH containing 0.15 eq Pemetrexed Monosodium and 0% to 2% water (v/v) was heated at reflux until IPC-PXRD showed complete transformation to Pemetrexed Disodium Form IV. Then 0.15 eq NaOH were added and stirring under reflux was continued for 2 h followed by hot filtration. The wet product was washed with EtOH and dried in vacuo at 50° C. at 5 mbar to constant weight to give Pemetrexed Disodium Form IV.

In particular, the conversion of Pemetrexed Disodium Heptahydrate to Pemetrexed Disodium Form IV was achieved by the following protocoll.

A suspension of Pemetrexed Disodium Heptahydrate (1.0 g, 1.67 mmol) and Pemetrexed Monosodium (0.10 g, 7.8% $H_2O$ (KFT)) in a mixture of EtOH (16.3 mL) and water (0.17 g) was stirred under reflux for 16 h. aq. NaOH solution (0.027 g, 30% w/w) was added and stirring under reflux was continued for 2 h before hot filtration at IT=68° C. to 78° C. The filter cake was washed with hot EtOH (10 mL, containing 1% water v/v) and the wet product was dried at 60° C. in vacuum for 16 h. Obtained polymorphic form: Pemetrexed Disodium Form IV. Yield: 0.81 g, $HClO_4$ titration: 97.7%, $H_2O$: 1.8%.

c) Attempted Conversion of Pemetrexed Disodium Form A to Pemetrexed Disodium Form IV in the Presence of Seeding Crystals of Pemetrexed Disodium Form IV A suspension of Pemetrexed Disodium Form A in EtOH containing seeding crystals of Pemetrexed Disodium Form IV and 0% to 2% water (v/v) was heated to reflux for 16 h. The suspension was cooled to 20° C. to 30° C. followed by filtration. The wet product was washed with EtOH and dried in vacuo at 50° C. at 5 mbar to constant weight to give Pemetrexed Disodium Form A.

d) Conversion of Pemetrexed Disodium Form A to Pemetrexed Disodium Form IV

The conversion of Pemetrexed Disodium Form A to Pemetrexed Disodium Form IV may be achieved with and without the use of seed crystals, in particular Pemetrexed Monosodium.

With Pemetrexed Monosodium:

A suspension of Pemetrexed Disodium Form A in EtOH containing 0.15 eq Pemetrexed Monosodium and 0% to 2% water (v/v) was heated to reflux until transformation to Pemetrexed Disodium Form IV was complete according to PXRD. 0.15 eq NaOH were added and stirring under reflux was continued for 2 h followed by hot filtration. The wet product was washed with EtOH and dried in vacuo to constant weight to give Pemetrexed Disodium Form IV.

Without Pemetrexed Monosodium:

A suspension of Pemetrexed Disodium Form A (15 g, 97.5% assay (corr. by 2.5% $H_2O$ (KFT), 31.0 mmol) in a mixture of EtOH (236.7 g) and water (6.23 g) was stirred at IT=75° C. to 78° C. (reflux) for 16 h before hot filtration at IT=65° C. to 75° C. The filter cake was washed with EtOH (100 mL, IT=20° C. to 30° C.) and the wet product was dried at 50° C. in vacuo to constant weight. Pemetrexed Disodium Form IV was obtained as white to off-white powder. 13 g, 98% assay (corr. by 1.2% water and 0.56% EtOH), 87% yield, 99.65% HPLC-purity.

e) Attempted Conversion of Pemetrexed Monosodium to Pemetrexed Disodium Form IV with Fast Addition of NaOH A suspension of Pemetrexed Monosodium in EtOH containing 0-2% water (v/v) was heated to reflux. 1.0 eq of aq. NaOH (30% w/w) were added within 1 min followed by seeding crystals of Pemetrexed Disodium Form IV and the mixture was stirred at reflux for 16 h before the suspension was cooled to 20° C. to 30° C. The solid was isolated by filtration, washed with EtOH and dried in vacuo at 50° C. at 5 mbar to constant weight to give Pemetrexed Disodium Form A.

f) Conversion of Pemetrexed Monosodium to Pemetrexed Disodium Form IV with Portionwise Addition of NaOH A suspension of Pemetrexed Monosodium in EtOH containing 0-2% water (v/v) was heated to reflux and 0.85 eq of aq. NaOH (30% w/w) were added. The mixture was stirred at reflux until PXRD showed complete conversion. 0.15 eq of aq. NaOH (30% w/w) were added and stirring under reflux was continued for 2 h before the suspension was cooled to 20° C. to 30° C. Pemetrexed Disodium Form IV was isolated by filtration, washed with EtOH and dried in vacuo at 50° C. at 5 mbar to constant weight.

In particular, the conversion of Pemetrexed Monosodium to Pemetrexed Disodium Form IV was achieved by the following protocoll.

At IT=75° C. to 80° C. under $N_2$-atmosphere aq. NaOH solution (2.34 g, 30% w/w, 0.85 eq) was added to a degassed suspension of Pemetrexed Monosodium (10.0 g, 20.0 mmol, 6.8% water (KFT)) in EtOH (110.2 g). The resulting mixture was stirred at IT=75° C. to 80° C. until IPC-PXRD indicated complete conversion to Pemetrexed Disodium Form IV. Then at IT=75° C. to 80° C. aq. NaOH solution (0.42 g, 30%, 0.15 eq) was added and the resulting mixture was cooled to IT=0° C. to 10° C. and stirred at this IT for 1 h before filtration under $N_2$-atmosphere. The wet product was washed with EtOH (80 g) and dried at 60° C., 5 mbar to constant weight. Pemetrexed Disodium was obtained as white powder. 9.8 g, 99.25% assay ($HClO_4$ titration), 0.72% $H_2O$ (KFT), 0.02% chloride; Yield: 99.0% (based on $HClO_4$ titration assay).

g) Conversion of Pemetrexed Monosodium to Pemetrexed Disodium Form IV with Slow Addition of NaOH A suspension of Pemetrexed Monosodium in EtOH containing 0-2% water (v/v) was heated to reflux. 1.0 eq of aq. NaOH (30% w/w) were added over a period of 2 to 4 h and the mixture was stirred under reflux until PXRD showed complete conversion. The suspension was cooled to 20° C. to 30° C. and the solid was isolated by filtration, washed with EtOH and dried in vacuo to constant weight at 50° C. at 5 mbar to give Pemetrexed Disodium Form IV.

h) Attempted Conversion of Pemetrexed to Pemetrexed Disodium Form IV with Fast Addition of NaOH A suspension of Pemetrexed in EtOH containing 0% to 2% water (v/v) was heated to reflux and 2.0 eq of aq. NaOH (30% w/w) were added within 1 min. The mixture was stirred at reflux for 16 h before the suspension was cooled to 20° C. to 30° C. The solid was isolated by filtration, washed with EtOH and dried in vacuo to constant weight to give Pemetrexed Disodium Form A.

i) Conversion of Pemetrexed to Pemetrexed Disodium Form IV with Portionwise Addition of NaOH A suspension of Pemetrexed in EtOH containing 0% to 2% water (v/v) is heated to reflux and 1.85 eq of aq. NaOH (30% w/w) are added. The mixture is stirred at reflux until PXRD shows complete conversion. 0.15 eq of aq. NaOH (30% w/w) are added and stirring under reflux is continued for 2 h before the suspension is cooled to 20° C. to 30° C. Pemetrexed Disodium Form IV is isolated by filtration, washed with EtOH and dried in vacuo to constant weight.

Stability Study of Pemetrexed Disodium Heptahydrate, 2.5 Hydrate, Form A and Form IV Preparation of Samples for Stability Investigations To investigate the stability of the different forms of Pemetrexed Disodium a stability test concerning storage at different relative humidity, storage in the presence of light and stability under drying conditions was carried out.

| Polymorphic form | Heptahydrate | 2.5 hydrate | Form A | Form IV |
|---|---|---|---|---|
| Aspect | Slightly beige | Slightly beige | Slightly beige | Slightly beige |
| HPLC-purity (10.5 min) | 99.90% | 99.86% | 99.59% | 99.85% |
| H$_2$O (KFT) | 21.19%/ 21.19% | 8.99%/ 9.00% | 1.82%/ 1.59% | 0.88%/ 0.86% |
| EtOH (ppm) | 261/ 264 | 334/ 283 | 1882/ 1852 | 3864/ 4066 |
| Titration (HClO$_4$) | 79.32%/ 79.33% | 91.34%/ 91.12% | 97.98%/ 97.64% | 97.27%/ 97.19% |
| PXRD | Heptahydrate + traces 2.5 hydrate | 2.5 hydrate | Form A | Form IV |

Pemetrexed Disodium Starting Materials for Stability Studies

Stability Upon Vacuum Drying at 70° C.

Four samples were stored at 70° 5 mbar in laboratory vacuum oven. IPC were taken after 2 d, 9 d

TABLE 1

In process controls of Pemetrexed Disodium stability of polymorphic forms at 70° C., 5 mbar

| Polymorphic form | Heptahydrate | 2.5 hydrate | Form A | Form IV |
|---|---|---|---|---|
| Time of drying (1$^{st}$ IPC) | 2 d | 2 d | 2 d | 2 d |
| Aspect | Slightly beige | Slightly beige | Slightly beige | Slightly beige |
| HPLC-purity (10.5 min) | 99.86% | 99.88% | 99.67% | 99.70% |
| H$_2$O (KFT) | 8.36%/ 8.57% | 8.75%/ 8.74% | 2.35%/ 2.52% | 0.94%/ 0.94% |
| PXRD | 2.5 hydrate | 2.5 hydrate | Form A | Form IV |
| Time of drying (2$^{nd}$ IPC) | 9 d | 9 d | 9 d | 9 d |
| Aspect | Slightly beige | Slightly beige | beige | Slightly beige |
| HPLC-purity (10.5 min) | 99.80% | 99.80% | 99.41 | 99.80 |
| H$_2$O (KFT) | 6.11%/ 6.13% | 7.71%/ 8.15% | 3.94%/ 3.88% | 1.22%/ 0.95% |

Stability Upon Storage at Different Relative Humidity

Stability Upon Storage at 5% to 12% Relative Humidity

The samples were stored in a desiccator in the dark under air atmosphere at IT=20° C. to 25° C. in a relative humidity of 5% to 12% (storage over a saturated solution of KOH). IPC were taken after 2 d, 5 d, 9 d and 16 d.

TABLE 2

In process controls of Pemetrexed Disodium stability of polymorphic forms at 5% to 12% relative humidity

| Polymorphic form | Heptahydrate | 2.5 hydrate | Form A | Form IV |
|---|---|---|---|---|
| Time of storage (1$^{st}$ IPC) | 2 d | 2 d | 2 d | 2 d |
| Relative humidity | 11.7% | 11.7% | 5.8% | 11.7% |
| (temperature) | (23° C.) | (23° C.) | (23° C.) | (23° C.) |
| Aspect | Slightly beige | Slightly beige | Slightly beige | Slightly beige |
| HPLC-purity (10.5 min) | 99.70% | 99.74% | 99.59% | 99.66% |
| H$_2$O (KFT) | 19.7% | 8.9% | 3.5% | 1.0% |
| PXRD | Heptahydrate + traces 2.5 hydrate | 2.5 hydrate | Form A | Form IV |
| Time of storage (2$^{nd}$ IPC) | 5 d | 5 d | 5 d | 5 d |
| Relative humidity | 9.5% | 9.5% | 5.3% | 9.5% |
| (temperature) | (24° C.) | (24° C.) | (24° C.) | (24° C.) |
| Aspect | Slightly beige | Slightly beige | Slightly beige | Slightly beige |
| HPLC-purity (10.5 min) | 99.73% | 99.82% | 99.33% | 99.60% |
| H$_2$O (KFT) | 15.63%/ 15.86% | 8.76%/ 8.66% | 3.33%/ 3.18% | 1.04%/ 0.94% |
| PXRD | Heptahydrate, traces 2.5 hydrate | 2.5 hydrate | Form A | Form IV |
| Time of storage (3$^{rd}$ IPC) | 9 d | 9 d | 9 d | 9 d |
| Relative humidity | 9% | 9% | 6% | 9% |
| (temperature) | (24° C.) | (24° C.) | (24° C) | (24° C.) |
| Aspect | Slightly beige | Slightly beige | Slightly beige | Slightly beige |
| HPLC-purity (10.5 min) | 99.86% | 99.90% | 99.58% | 99.83% |
| H$_2$O (KFT) | 13.68%/ 13.71% | 9.08%/ 9.05% | 3.96%/ 4.06% | 1.42%/ 1.43% |
| PXRD | Heptahydrate + 2.5 hydrate | 2.5 hydrate | Form A | Form IV |
| Time of storage (4$^{th}$ IPC) | 16 d | 16 d | 16 d | 16 d |
| Relative humidity | 8.5% | 8.5% | 5.8% | 8.5% |
| (temperature) | (24° C.) | (24° C.) | (24° C.) | (24° C.) |
| Aspect | Slightly beige | Slightly beige | Slightly beige | Slightly beige |
| HPLC-purity | 99.88% | 99.80 | 99.50% | 99.88% |
| H$_2$O (KFT) | 12.09%/ 12.12% | 9.02%/ 9.03% | 3.66%/ 3.64% | 1.30%/ 1.15% |
| PXRD | 2.5 hydrate + traces Heptahydrate | 2.5 hydrate | Form A | Form IV |

Stability Upon Storage at 27% to 33% Relative Humidity

The samples were stored in a desiccator in the dark under air atmosphere at IT=20° C. to 25° C. in a relative humidity of 27% to 33% (storage over a saturated solution of MgCl$_2$). IPC were taken after 2 d, 5 d, 9 d and 16 d.

TABLE 3

In process controls of Pemetrexed Disodium stability of polymorphic forms at 27% to 33% relative humidity

| Polymorphic form | Heptahydrate | 2.5 hydrate | Form A | Form IV |
|---|---|---|---|---|
| Time of storage (1$^{st}$ IPC) | 2 d | 2 d | 2 d | 2 d |
| Relative humidity | 29.8% | 29.8% | 28% | 29.8% |
| (temperature) | (23° C.) | (23° C.) | (23° C.) | (23° C.) |
| Aspect | Slightly beige | Slightly beige | Slightly beige | Slightly beige |
| HPLC-purity | 99.74% | 99.82% | 99.60% | 99.81% |
| H$_2$O (KFT) | 21.83%/ 21.84% | 9.00%/ 8.98% | 6.53%/ 6.52% | 1.40%/ 1.37% |
| PXRD | Heptahydrate, traces 2.5 hydrate | 2.5 hydrate | Form A (turned yellow) | Form IV |

TABLE 3-continued

In process controls of Pemetrexed Disodium stability of polymorphic forms at 27% to 33% relative humidity

| Polymorphic form | Heptahydrate | 2.5 hydrate | Form A | Form IV |
|---|---|---|---|---|
| Time of storage (2$^{nd}$ IPC) | 5 d | 5 d | 5 d | 5 d |
| Relative humidity (temperature) | 29% (24° C) | 29% (24° C.) | 27% (24° C.) | 29% (24° C.) |
| Aspect | Slightly beige | Slightly beige | Slightly beige | Slightly beige |
| HPLC-purity | 99.62% | 99.91% | 99.43% | 99.73% |
| H$_2$O (KFT) | 20.87%/ 20.18% | 9.17%/ 9.01% | 6.41%/ 6.56% | 1.38%/ 1.34% |
| PXRD | Heptahydrate, traces 2.5 hydrate | 2.5 hydrate | Form A | Form IV |
| Time of storage (3$^{rd}$ IPC) | 9 d | 9 d | 9 d | 9 d |
| Relative humidity (temperature) | 31% (24° C.) | 31% (24° C.) | 30% (24° C.) | 31% (24° C.) |
| Aspect | Slightly beige | Slightly beige | Slightly beige | Slightly beige |
| HPLC-purity | 99.84% | 99.84% | 99.57% | 99.82% |
| H$_2$O (KFT) | 21.15%/ 21.21% | 9.59%/ 9.57% | 7.14%/ 7.16% | 1.70%/ 1.67% |
| PXRD | Heptahydrate, traces 2.5 hydrate | 2.5 hydrate + traces Heptahydrate | Form A | Form IV |
| Time of storage (4$^{th}$ IPC) | 16 d | 16 d | 16 d | 16 d |
| Relative humidity (temperature) | 30.4% (24° C.) | 30.4% (24° C.) | 28.7% (24° C.) | 30.4% (24° C.) |
| Aspect | Slightly beige | Slightly beige | Slightly beige | Slightly beige |
| HPLC-purity | 99.91% | 99.64% | 99.69% | 99.86% |
| H$_2$O (KFT) | 21.21%/ 21.21% | 10.09%/ 10.11% | 6.94%/ 7.01% | 1.46%/ 1.41% |
| PXRD | Heptahydrate | 2.5 hydrate + traces Heptahydrate | Form A | Form D |

Stability Upon Storage at 39% to 50% Relative Humidity

The samples were stored in a desiccator in the dark under air atmosphere at IT=20° C. to 25° C. in a relative humidity of 39% to 50% (storage over a saturated solution of Ca(NO$_3$)$_2$). IPC were taken after 2 d, 5 d, 9 d and 16 d.

TABLE 4

In process controls or Pemetrexea Disodium stability or polymorphic forms at 39% to 50% relative humidity.

| Polymorphic form | Heptahydrate | 2.5 hydrate | Form A | Form IV |
|---|---|---|---|---|
| Time of storage (1$^{st}$ IPC) | 2 d | 2 d | 2 d | 2 d |
| Relative humidity (temperature) | 41.1% (23° C.) | 41.1% (23° C.) | 39% (23° C.) | 41.1% (23° C.) |
| Aspect | Slightly beige | Slightly beige | Slightly beige | Slightly beige |
| HPLC-purity | 99.84% | 99.83% | 99.68% | 99.84% |
| H$_2$O (KFT) | 20.84%/ 20.95% | 14.67%/ 14.13% | 8.22%/ 8.31% | 1.65%/ 1.68% |
| PXRD | Heptahydrate, traces 2.5 hydrate | Hepta + 2.5 hydrate | Form A | Form IV |
| Time of storage (2$^{nd}$ IPC) | 5 d | 5 d | 5 d | 5 d |
| Relative humidity (temperature) | 42.8% (24° C.) | 42.8% (24° C.) | 38.6% (24° C.) | 42.8% (24° C.) |
| Aspect | Slightly beige | Slightly beige | Slightly beige | Slightly beige |
| HPLC-purity | 99.78% | 99.62% | 99.64% | 99.78% |
| H$_2$O (KFT) | 20.63%/ 20.58% | 20.21%/ 20.47% | 10.59%/ 10.56% | 1.80%/ 1.79% |
| PXRD | Heptahydrate | Heptahydrate | Form A | Form IV |
| Time of storage (3$^{rd}$ IPC) | 9 d | 9 d | 9 d | 9 d |
| Relative humidity (temperature) | 48% (24° C.) | 48% (24° C.) | 47% (24° C.) | 48% (24° C.) |
| Aspect | Slightly beige | Slightly beige | Slightly beige | Slightly beige |
| HPLC-purity | 99.81% | 99.74% | 99.62% | 99.76% |
| H$_2$O (KFT) | 21.21%/ 21.20% | 21.14%/ 21.33% | 12.51%/ 12.60% | 3.10%/ 3.02% |
| PXRD | Heptahydrate | Heptahydrate | Form A | Form IV |
| Time of storage (4$^{th}$ IPC) | 16 d | 16 d | 16 d | 16 d |
| Relative humidity (temperature) | 47.3% (24° C.) | 47.3% (24° C.) | 46.4% (24° C.) | 47.3% (24° C.) |
| Aspect | Slightly beige | Slightly beige | Slightly beige | Slightly beige |
| HPLC-purity | 99.91% | 99.86% | 99.70% | 99.81% |
| H$_2$O (KFT) | 21.47%/ 21.43% | 21.39%/ 21.48% | 12.73%/ 13.17% | 5.51%/ 5.54% |
| PXRD | Heptahydrate | Heptahydrate | Form A | Form IV + traces Heptahydrate |

Stability Upon Storage at 60% to 70% Relative Humidity

The samples were stored in a desiccator in the dark under air atmosphere at IT=20° C. to 25° C. in a relative humidity of 60% to 70% (storage over a saturated solution of NaCl). IPC were taken after 2 d, 5 d, 9 d and 16 d.

TABLE 5

In process controls of Pemetrexed Disodium stability of polymorphic forms at 60% to 70% relative humidity

| Polymorphic form | Heptahydrate | 2.5 hydrate | Form A | Form IV |
|---|---|---|---|---|
| Time of storage (1$^{st}$ IPC) | 2 d | 2 d | 2 d | 2 d |
| Relative humidity (temperature) | 61% (22° C.) | 61% (22° C.) | 54% (23° C) | 61% (22° C.) |
| Aspect | Slightly beige | Slightly beige | Slightly beige | Slightly beige |
| HPLC-purity | 99.63% | 99.73% | 99.71% | 99.83% |
| H$_2$O (KFT) | 20.96%/ 20.95% | 20.71%/ 20.75% | 15.75%/ 15.70% | 8.53%/ 8.41% |
| PXRD | Heptahydrate + traces 2.5 hydrate | Heptahydrate | Form A | Form IV + Heptahydrate |
| Time of storage (2$^{nd}$ IPC) | 5 d | 5 d | 5 d | 5 d |
| Relative humidity | 63% | 63% | 57% | 63% |

TABLE 5-continued

In process controls of Pemetrexed Disodium stability
of polymorphic forms at 60% to 70% relative humidity

| Polymorphic form | Heptahydrate | 2.5 hydrate | Form A | Form IV |
|---|---|---|---|---|
| (temperature) | (24° C.) | (24° C.) | (24° C.) | (24° C.) |
| Aspect | Slightly beige | Slightly beige | Slightly beige | Slightly beige |
| HPLC-purity | 99.81% | 99.86% | 99.51% | 99.75% |
| H$_2$O (KFT) | 20.89%/ 20.35% | 20.53%/ 20.78% | 21.85%/ 21.88% | 20.03%/ 20.12% |
| PXRD | Heptahydrate | Heptahydrate | Form A | Heptahydrate |
| Time of storage (3$^{rd}$ IPC) | 9 d | 9 d | 9 d | 9 d |
| Relative humidity | 69% | 69% | 68% | 69% |
| (temperature) | (24° C.) | (24° C.) | (24° C.) | (24° C.) |
| Aspect | Slightly beige | Slightly beige | Slightly beige | Slightly beige |
| HPLC-purity | 99.81% | 99.84% | 99.71% | 99.85% |
| H$_2$O (KFT) | 21.27%/ 21.3% | 21.41%/ 21.37% | 21.56%/ 21.61% | 20.85%/ 20.96% |
| PXRD | Heptahydrate | Heptahydrate | Heptahydrate | Heptahydrate |
| Time of storage (4$^{th}$ IPC) | 16 d | 16 d | 16 d | 16 d |
| Relative humidity | 66.9% | 66.9% | 67.2% | 66.9% |
| (temperature) | (24° C.) | (24° C.) | (24° C.) | (24° C.) |
| Aspect | Slightly beige | Slightly beige | Slightly beige | Slightly beige |
| HPLC-purity | 99.90% | 99.83% | 99.72% | 99.81% |
| H$_2$O (KFT) | 21.46%/ 21.57% | 21.72%/ 21.58% | 21.60%/ 21.73% | 20.83%/ 20.83% |
| PXRD | Heptahydrate | Heptahydrate | Heptahydrate | Heptahydrate |

Stability in the Presence of Light

The samples were stored in double PE plastic bags and exposed to daylight IT=20° C. to 25° C. IPCs were taken after 15 d.

TABLE 6

In process controls of Pemetrexed Disodium stability
of polymorphic forms in the presence of light.

| Polymorphic form | Heptahydrate | 2.5 hydrate | Form A | Form IV |
|---|---|---|---|---|
| Time of storage | Start | Start | Start | Start |
| Aspect | Slightly beige | Slightly beige | Slightly beige | Slightly beige |
| HPLC-purity | 99.63% | 99.73% | 99.71% | 99.83% |
| H$_2$O (KFT) | 21.19%/ 21.19% | 8.99%/ 9.00% | 1.82%/ 1.59% | 0.88%/ 0.86% |
| Time of storage (1$^{st}$ IPC) | 15 d | 15 d | 15 d | 15 d |
| Aspect | Slightly beige | Slightly beige | beige | Slightly beige |
| HPLC-purity | 99.65% | 99.74% | 95.83% | 99.44% |
| H$_2$O (KFT) | 20.14%/ 19.18% | 10.40%/ 10.11% | 2.44% | 1.69%/ 1.65% |

Discussion of Results

Stability Upon Vacuum Drying

Pemetrexed Disodium Heptahydrate is transformed to Pemetrexed Disodium 2.5 hydrate upon vacuum drying (PXRD shows only 2.5 hydrate after 2 d, water content 8.4% after 2 d). No significant change in HPLC-purity.

Pemetrexed Disodium 2.5 hydrate shows a decreased water content to 7.9% after 9 d. Within 9 days no significant change in HPLC-purity is observed.

Pemetrexed Disodium Form A shows a significant decrease in HPLC-purity after 9 d (formation of unknown impurities).

Pemetrexed Disodium Form IV shows no significant change in HPLC-purity or water content after 9 d.

Stability Upon Storage at Different Relative Humidity

Pemetrexed Disodium Heptahydrate is not stable upon storage at 5% to 12% rel. humidity (PXRD shows almost complete transformation to Pemetrexed Disodium 2.5 hydrate within 16 days). At 27% to 33%, 40% to 50% and 60% to 70% relative humidity Pemetrexed Disodium Heptahydrate is stable up to 16 d. No significant change in HPLC purity is observed in any of the samples.

Pemetrexed Disodium 2.5 hydrate shows no significant change in PXRD, HPLC-purity or water content at 5% to 12% rel. humidity. After 9 d at 27% to 33% relative humidity PXRD shows traces of Pemetrexed Disodium Heptahydrate together with a slight increase of water content. After 2 days at 40% to 50% PXRD already shows formation of Pemetrexed Disodium Heptahydrate, together with an increase of water content. After 5 d the transformation seems to be complete. At 60% to 70% rel. humidity transformation to Pemetrexed Disodium Heptahydrate is complete after 2 d. No significant change in HPLC purity is observed in any of the samples.

Pemetrexed Disodium Form A does not show a significant change in PXRD, water content or HPLC-purity after 16 d at 7% to 12% rel. humidity. At 27% to 33% and 40% to 50% rel. humidity a significant in increase in water content is detected without visible change in PXRD or HPLC-purity after 16 d. At 60% to 70% rel. humidity complete transformation to Pemetrexed Disodium Heptahydrate is observed after 9 d without significant change in HPLC-purity.

Pemetrexed Disodium Form IV does not show significant change in PXRD or water content after 16 d at 7% to 12% and 27% to 33% rel. humidity. After 9 d at 40% to 50% rel. humidity a slight increase in water content is observed without significant change in PXRD, after 16 d traces of Pemetrexed Disodium Heptahydrate are identifiable in PXRD. After 2 d at 60% to 70% rel. humidity already partial transformation to Pemetrexed Disodium Heptahydrate is observed in PXRD, together with significant increase in water content. Transformation to Pemetrexed Disodium Heptahydrate is complete after 5 d. No significant change in HPLC purity is observed in any of the samples.

Stability Upon Storage in the Presence of Light

Pemetrexed Disodium Heptahydrate and Pemetrexed Disodium 2.5 hydrate do not show significant changes regarding HPLC purity or color. Pemetrexed Disodium Form A after 16 d already shows significant formation of color and a lot of decomposition products are visible in HPLC chromatogram. Pemetrexed Disodium Form IV after 16 d shows a slight decrease in HPLC-purity without significant change in color.

Conclusion

Pemetrexed Disodium Heptahydrate was found to be not stable upon vacuum drying and is not stable at low relative humidity (<12%). In both cases formation of Pemetrexed Disodium 2.5 hydrate was observed. Pemetrexed Disodium 2.5 hydrate is not stable at higher relative humidity (already after 9 d at 27% to 33% rel. humidity partial transformation to Pemetrexed Disodium Heptahydrate is observed), indicating a hygroscopic character. Pemetrexed Disodium Form A is not stable upon prolonged vacuum drying (formation of unknown impurities) and seems to be highly hygroscopic (uptake of 21% water at 60% to 70% rel. humidity) leading finally to transformation to Pemetrexed Disodium Heptahydrate. Furthermore, already after 16 d Pemetrexed Disodium Form A shows significant decomposition and color change in the presence of light. Surprisingly is was found that Pemetrexed Disodium Form IV is more stable upon drying compared to Pemetrexed Disodium Heptahydrate (no change in PXRD) or Pemetrexed Disodium Form A (no significant change in HPLC-purity). Furthermore it is stable in a wide range of relative humidity for a short period of time (up to 9 d at 50%) and only at high relative humidity (>60%) it shows transformation to Pemetrexed Disodium Heptahydrate. Another surprising characteristic of Pemetrexed Disodium Form IV is its relatively low hygroscopic character compared to Pemetrexed Disodium 2.5 hydrate or Pemetrexed Disodium Form A. Furthermore, Pemetrexed Disodium Form IV was found to be more stable towards light than Pemetrexed Disodium Form A.

Analytics

HPLC analysis was done on an Agilent 1100 system equipped with DAD detector using a Zorbax SB-Phenyl column (150×4.6 mm, 3 μm). Measurements were done at 230 nm wavelengths at 25° C. using a flow of 1.0 mL/min and 8 min post-run time. As mobile phase water containing 0.03% TFA and acetonitrile containing 0.025% TFA were used, solvents were HPLC grade. Sample preparation: 10 mg sample in 25 mL water:ACN=1:1, 5 uL injection. Retention time Pemetrexed Disodium: 10.3 min.

| Gradient: | | | |
|---|---|---|---|
| Time [min] | 0.03% TFA in water [%] | 0.025% TFA in ACN [%] | Flow rate [mL/min] |
| 0 | 90 | 10 | 1.0 |
| 3 | 90 | 10 | 1.0 |
| 35 | 20 | 80 | 1.0 |
| 12 | 64 | 36 | 1.0 |
| 20 | 64 | 36 | 1.0 |
| 25 | 60 | 40 | 1.0 |
| 30 | 53 | 47 | 1.0 |
| 32 | 20 | 80 | 1.0 |
| 35 | 20 | 80 | 1.0 |

Chiral HPLC analysis was done on an Agilent 1100 system equipped with DAD detector using a Chirobiotic T column (100×4.6 mm, 5 um). Measurements were done at 225 nm wavelengths at 20° C. using a flow of 0.5 mL/min. Sample preparation: 10 mg sample in 10 mL MeOH:EtOH=9:1, 5 uL injection. Mobile phase: MeOH+0.2% CH3COOH+0.1% Triethyl amine, run time: 20 min (isocratic). Retention times: Pemetrexed-L-isomer: 5.4 min, Pemetrexed-D-isomer: 8.3 min.

$HClO_4$ titrations were carried out using Metrohm 751 GPD Titrino system equipped with Metrohm 727 Ti Stand and 6.0229.100 Solvotrode (for non-aqueous titrations). 100 mg sample were dissolved in 80 mL glacial acetic acid (p.a. quality) and titrated using 0.1N HClO4.

NaOH titrations were carried out using Metrohm 751 GPD Titrino system equipped with Metrohm 727 Ti Stand and 60238.000 combined pH electrode. 100 mg sample were dissolved in 10 mL DMSO (p.a. quality) before dilution with 70 mL water. Titration was done using 0.1N NaOH.

KFT: Karl-Fischer titrations titration was carried out using Metrohm 751 GPD Titrino system equipped with 703 Ti stand and 6.0338.100 double Pt-electrode. 100 mg sample were dissolved in previously dried methanol and titration was done using KF reagent Hydranal Composite 2 (Fluka 34806).

PXRD: Routine PXRD measurements were carried out on a Bruker AXS D8Advance diffractometer equipped with CuKα source with $CuK_β$ filter and a VANTEC detector (Ser. No.: 202964). Measurement parameters: 3° 2theta to 39.9° 2theta, step time: 2s, step size: 0.022°, T=25° C., X-ray generator: 35 kV/40 mA.

DSC measurements: Mettler Toledo DSC821e.

FT-IR measurements: Jasco FT/IR-6100 equipped with a Specar ATR unit.

The invention claimed is:

1. Crystalline form of Pemetrexed Disodium which has characteristic reflexes in an X-ray powder diffractogram using CuKα radiation with Cukβ filter at a 2θ angle: 7.7±0.2, 9.7±0.2, 18.6±0.2, 19.2±0.2, 20.4±0.2, 24.3±0.2, 26.6±0.2, 28.7±0.2, 28.9±0.2, and 30.0±0.2.

2. The crystalline form of Pemetrexed Disodium according to claim 1, wherein the X-ray powder diffractogram also shows characteristic reflexes selected from the group consisting of 5.5±0.2, 10.9±0.2, 13.0±0.2, 13.6±0.2, and 21.8±0.2.

3. The crystalline form of Pemetrexed Disodium according to claim 1, wherein the X-ray powder diffractogram also shows at least 20 of the characteristic reflexes selected from the group consisting of 5.5±0.2, 7.7±0.2, 9.2±0.2, 9.7±0.2, 10.9±0.2, 13.0±0.2, 13.6±0.2, 15.3±0.2, 16.0±0.2, 16.7±0.2, 17.0±0.2, 18.1±0.2, 18.6±0.2, 19.2±0.2, 20.0±0.2, 20.4±0.2, 21.8±0.2, 22.3±0.2, 22.7±0.2, 23.0±0.2, 24.3±0.2, 25.9±0.2, 26.6±0.2, 27.0±0.2, 27.2±0.2, 28.0±0.2, 28.7±0.2, 28.9±0.2, 30.0±0.2, 30.8±0.2, 31.5±0.2, 32.0±0.2, 33.6±0.2, 34.2±0.2, 34.6±0.2, 35.0±0.2, 36.2±0.2, 37.1±0.2, 37.9±0.2, 38.2±0.2, 38.9±0.2, and 39.4±0.2.

4. The crystalline form of Pemetrexed Disodium according to claim 1, wherein the X-ray powder diffractogram corresponds to the X-ray powder diffractogram shown in FIG. 1a and/or FIG. 1b.

5. The crystalline form of Pemetrexed Disodium according to claim 1, wherein said crystalline form has a Differential Scanning Calorimetry (DSC) corresponds to the DSC spectra shown in FIG. 3.

6. Pharmaceutical composition comprising Pemetrexed Disodium according to claim 1 together with a pharmaceutical acceptable carrier, diluent and/or excipient.

7. A method for the inhibition of the folate metabolic Pathway, thymidylate synthase, dihydrofolate reductase and/or glycinamide ribonucleotide formyl transferase, comprising administering the pharmaceutical composition according to claim 6 to a patient in need of such treatment.

8. The method according to claim 7 wherein said patient is suffering from cancer.

9. The pharmaceutical composition according to claim 6 comprising a further active agent.

10. A method for inhibiting, the folate metabolic pathway, thymidylate synthase, dihydrofolate reductase and/or glycinamide ribonucleotide formyl transferase, comprising administering to a patient in need of such treatment, a crystalline form of Pemetrexed Disodium which has a property of characteristic reflexes in an X-ray powder diffractogram using CuKα radiation with Cukβ filter at a 2θ angle: 7.7±0.2, 9.7±0.2, 18.6±0.2, 19.2±0.2, 20.4±0.2, 24.3±0.2, 26.6±0.2, 28.7±0.2, 28.9±0.2, and 30.0±0.2.

11. The method of claim 10 wherein said patient is suffering from cancer.

12. Process for the preparation of Pemetrexed Disodium according to claim 1 comprising the steps
    (a) providing a mixture of Pemetrexed Disodium in a solvent comprising 0% to 5% $H_2O$ (v/v),
    (b) addition of seeding crystals,
    (c) heating under reflux until transformation to Pemetrexed Disodium according to claim 1 is complete, and
    (d) isolation of the product,
    or
    (a') providing Pemetrexed Monosodium in a solvent, comprising 0% to 5% $H_2O$ (v/v),
    (b') slow or portionwise addition of about 0.5 to 1.5 mole equivalents of NaOH,
    (c') heating under reflux until transformation to Pemetrexed Disodium according to claim 1 is complete, and
    (d') isolation of the product,
    or
    (a") providing Pemetrexed in a solvent, comprising 0% to 5% $H_2O$ (v/v),
    (b") slow or portionwise addition of about 1.0 to 3.0 mole equivalents of NaOH,
    (c") heating under reflux transformation to Pemetrexed Disodium according to claim 1 is complete, and
    (d") isolation of the product.

13. The process according claim 12, wherein the seed crystals of step (b) are of Pemetrexed Monosodium.

14. A method of inhibiting the folate metabolic pathway of a patient in need of such inhibition, comprising administering an effective amount of Pemetrexed Disodium of claim 1 to said patient.

15. The method of claim 11, wherein said cancer is a solid tumor.

16. The crystalline form of Pemetrexed Disodium according to claim 3, wherein the X-ray powder diffractogram shows all of the characteristic reflexes selected from the group consisting of 5.5±0.2, 7.7±0.2, 9.2±0.2, 9.7±0.2, 10.9±0.2, 13.0±0.2, 13.6±0.2, 15.3±0.2, 16.0±0.2, 16.7±0.2, 17.0±0.2, 18.1±0.2, 18.6±0.2, 19.2±0.2, 20.0±0.2, 20.4±0.2, 21.8±0.2, 22.3±0.2, 22.7±0.2, 23.0±0.2, 24.3±0.2, 25.9±0.2, 26.6±0.2, 27.0±0.2, 27.2±0.2, 28.0±0.2, 28.7 ±0.2, 28.9±0.2, 30.0±0.2, 30.8±0.2, 31.5±0.2, 32.0±0.2, 33.6±0.2, 34.2±0.2, 34.6±0.2, 35.0±0.2, 36.2±0.2, 37.1±0.2, 37.9±0.2, 38.2±0.2, 38.9±0.2, and 39.4±0.2.

17. The process according claim 13, wherein the seed crystals of step (b) are Pemetrexed Monosodium in an amount of about 5 to 30 mol %.

18. The process according to claim 17, wherein the seed crystals of step (b) are Pemetrexed Monosodium in an amount of about 10 to 20 mol %.

19. The process according to claim 18, wherein the seed crystals of step (b) are Pemetrexed Monosodium in an amount of about 15 mol %.

20. The method according to claim 8, wherein said cancer is a solid tumor selected from the group consisting of malignant pleural mesothelioma and metastatic non-small cell lung cancer.

21. The process for the preparation of Pemetrexed Disodium according to claim 12, wherein the solvent is a $C_1$-$C_4$ alcohol comprising 1% to 4% $H_2O$ (v/v).

22. The process according to claim 21, wherein the solvent is EtOH comprising 1% to 3% $H_2O$ (v/v).

23. The process according to claim 12, wherein 0.7 to 1.3 mole equivalents of NaOH are added in step (b').

24. The process according to claim 23, wherein 0.8 to 1.1 mole equivalents of NaOH are added in step (b').

25. The process according to claim 24, wherein 1 mole equivalent of NaOH is added in step (b').

26. The process according to claim 12, wherein 1.7 to 2.3 mole equivalents of NaOH are added in step (b").

27. The process according to claim 26, wherein 1.8 to 2.1 mole equivalents of NaOH are added in step (b").

28. The process according to claim 27, wherein 2.0 mole equivalents of NaOH are added in step (b").

29. The crystalline form of Pemetrexed Disodium according to claim 1 which additionally has the property of characteristic signals in FT (Fourier-Transformation) Infrared spectra at 3469±2 $cm^{-1}$, 1691±2 $cm^{-1}$, 1640±2 $cm^{-1}$, 1576±2 $cm^{-1}$, 1490±2 $cm^{-1}$, 1454±2 $cm^{-1}$, 1409±2 $cm^{-1}$, 1393±2 $cm^{-1}$, 1287±2 $cm^{-1}$, and 676±2 $cm^{-1}$.

30. The method according to claim 10, wherein said crystalline form of Pemetrexed Disodium additionally has the property of characteristic signals in FT (Fourier-Transformation) Infrared spectra at 3469±2 cm−1, 1691±2 cm−1, 1640±2 cm−1, 1576±2 cm−1, 1490±2 cm−1, 1454±2 cm−1, 1409±2 cm−1, 1393±2 cm−1, 1287±2 cm−1, and 676±2 cm−1.

31. The crystalline form of Pemetrexed Disodium according to claim 29, wherein the FT-Infrared spectra also shows characteristic signals selected from the group consisting of 3306±2 cm−1, 1610±2 cm−1, 1228±2 cm−1, 903±2 cm−1, and 778±2 cm−1.

32. The crystalline form of Pemetrexed Disodium according to claim 29, wherein the FT-Infrared spectra shows the following characteristic signals at 3469±2 $cm^{-1}$, 3420±2 ce, 3407±2 $cm^{-1}$, 3388±2 $cm^{-1}$, 3306±2 $cm^{-1}$, 3206±2 $cm^{-1}$, 3098±2 $cm^{-1}$, 2925±2 $cm^{-1}$, 2901±2 $cm^{-1}$, 2867±2 $cm^{-1}$, 2752±2 $cm^{-1}$, 2364±2 $cm^{-1}$, 2355±2 $cm^{-1}$, 2323±2 $cm^{-1}$, 2292±2 $cm^{-1}$, 2165±2 $cm^{-1}$, 1984±2 $cm^{-1}$, 1691±2 $cm^{-1}$, 1640±2 $cm^{-1}$, 1610±2 $cm^{-1}$, 1576±2 $cm^{-1}$, 1530±2 $cm^{-1}$, 1520±2 $cm^{-1}$, 1490±2 $cm^{-1}$, 1454±2 $cm^{-1}$, 1409±2 $cm^{-1}$, 1393±2 $cm^{-1}$, 1349±2 $cm^{-1}$, 1287±2 $cm^{-1}$, 1249±2 $cm^{-1}$, 1227±2 $cm^{-1}$, 1212±2 $cm^{-1}$, 1181±2 $cm^{-1}$, 1161±2 $cm^{-1}$, 1149±2 $cm^{-1}$, 1140±2 $cm^{-1}$, 1105±2 $cm^{-1}$, 1092±2 $cm^{-1}$, 1081±2 $cm^{-1}$, 1040±2 $cm^{-1}$, 1018±2 $cm^{-1}$, 1000±2 ce, 950±2 $cm^{-1}$, 903±2 $cm^{-1}$, 876±2 $cm^{-1}$, 859±2 $cm^{-1}$, 846±2 $cm^{-1}$, 820 t 2 $cm^{-1}$, 778±2 $cm^{-1}$, 761±2 $cm^{-1}$, 741±2 $cm^{-1}$, 715±2 $cm^{-1}$, 706±2 $cm^{-1}$, 689±2 $cm^{-1}$, and 676±2 $cm^{-1}$.

33. The crystalline form of Pemetrexed Disodium according to claim 29, wherein the FT-Infrared spectra corresponds to the FT-Infrared spectra shown in FIG. 2*a* and/or FIG 2*b*.

* * * * *